United States Patent [19]

Nakaya et al.

[11] Patent Number: 5,021,412
[45] Date of Patent: Jun. 4, 1991

[54] THIADIAZINES, AND INSECTICIDAL AND ACARICIDAL PREPARATIONS

[75] Inventors: Michihiko Nakaya, Zushi; Yukiharu Fukushi, Sapporo; Kenji Kodaka, Yokohama; Masayuki Ooka, Yokohama; Shirou Shiraishi, Yokohama; Masahiko Nakamura, Yokohama; Satoshi Numata, Yokohama, all of Japan

[73] Assignee: Mitsui Toatsu Chemicals, Inc., Tokyo, Japan

[21] Appl. No.: 328,398

[22] Filed: Mar. 24, 1989

Related U.S. Application Data

[63] Continuation-in-part of Ser. No. 248,230, Sep. 23, 1988, abandoned.

[30] Foreign Application Priority Data

Sep. 25, 1987 [JP] Japan ................... 62-239002
Jul. 8, 1988 [JP] Japan ................... 63-168997
Jul. 14, 1988 [JP] Japan ................... 63-176063

[51] Int. Cl.$^5$ .................... A01N 43/88; C07D 285/34
[52] U.S. Cl. ........................... 514/223.8; 544/8
[58] Field of Search .................... 544/8; 514/223.8

[56] References Cited

U.S. PATENT DOCUMENTS 4,159,328 6/1979 Ikeda et al. ............. 514/223.8
4,452,795 6/1984 Farooq et al. ........... 514/223.8

FOREIGN PATENT DOCUMENTS 54-46794 4/1979 Japan .................. 514/223.8
54-154780 12/1979 Japan ................. 514/223.8

Primary Examiner—John M. Ford
Attorney, Agent, or Firm—Millen, White & Zelano

[57] ABSTRACT

Novel tetrahydro-1,3,5-thiadiazin-4-ones of the following general formula (I) or their salts which are useful as an insecticidal and acaricidal agent.

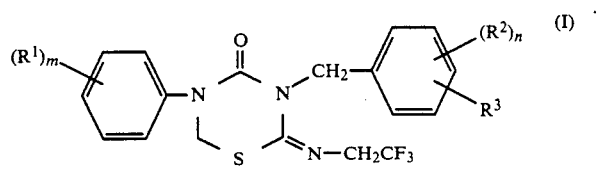

In the formula, each of $R^1$ and $R^2$ represents a halogen atom or a $C_1$-$C_4$ alkyl group; $R^3$ represents a halogen atom, a $C_1$-$C_4$ alkyl group, a $C_3$-$C_6$ cycloalkyl group, a $C_1$-$C_4$ alkoxy group, an acetyl group, a phenoxy group, a halo-substituted phenoxy group, a benzyl group, a benzyloxy group, a phenylcarbonyl group, a $C_1$-$C_4$ haloalkyloxy group, a $C_1$-$C_4$ haloalkyloxymethyl group, a $C_2$-$C_4$ haloalkenyloxy group, a $C_1$-$C_4$ haloalkylthio group, a $C_1$-$C_4$ haloalkylthiomethyl group, a $C_2$-$C_4$ haloalkenylthio group, a $C_1$-$C_8$ haloalkyl group, a $C_2$-$C_8$ haloalkenyl group, a $C_1$-$C_8$ alkyloxycarbonyl group, a substituted phenoxycarbonyl group, or a substituted pyridyloxy group; m represents 0, 1, 2 or 3; and n represents 0, 1, 2 or 3.

These novel thiadiazines are produced by reacting a compound of general formula (II)

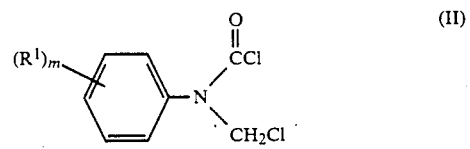

wherein $R^1$ and m are as defined above, with a compound of general formula (III)

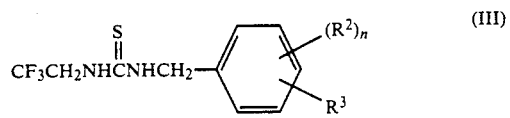

wherein $R^2$, $R^3$ and n are as defined above.

33 Claims, No Drawings

THIADIAZINES, AND INSECTICIDAL AND ACARICIDAL PREPARATIONS

This application is a continuation-in-part application of Ser. No. 248,230 filed on Sept. 23, 1988, now abandoned.

This invention relates to tetrahydro-1,3,5-thiadiazin-4-ones represented by the following general

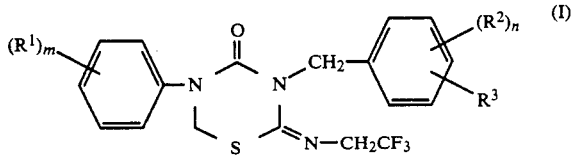

wherein each of $R^1$ and $R^2$ represents a halogen atom or a $C_1$-$C_4$ alkyl group; $R^3$ represents a halogen atom, a $C_1$-$C_4$ alkyl group, a $C_3$-$C_6$ cycloalkyl group, a $C_1$-$C_4$ alkoxy group, an acetyl group, a phenoxy group, a halo-substituted phenoxy group, a benzyl group, a benzyloxy group, a phenylcarbonyl group, a $C_1$-$C_4$ haloalkyloxy group, a $C_1$-$C_4$ haloalkyloxymethyl roup, a $C_2$-$C_4$ haloalkenyloxy group, a $C_1$-$C_4$ haloalkylthio group, a $C_1$-$C_4$ haloalkylthiomethyl group, a $C_2$-$C_4$ haloalkenylthio group, a $C_1$-$C_8$ haloalkyl group, a $C_2$-$C_8$ haloalkenyl group, a Cl-C8 alkyloxycarbonyl group, a substituted phenoxycarbonyl group, or a substituted pyridyloxy group; m represents 0, 1, 2 or 3; and n represents 0, 1, 2 or 3, or salts thereof; a process for production thereof; and to an insecticidal and acaricidal agent comprising at least one of the above compounds as an active ingredient.

The compounds of this invention are useful in various industrial fields, and particularly in the agricultural field as an insecticidal and acaricidal agent.

Japanese Laid-Open Patent Publications Nos. 1979, 12890/1979 and 154780/1979 state that tetrahydro-1,3,5-thiadiazin-4-ones have insecticidal and acaricidal activities.

Among them, 2-tertiary butylimino-3-isopropyl5-phenyl-tetrahydro-1,3,5-thiadiazin-4-one (common name: Buprofezin) represented by the following formula

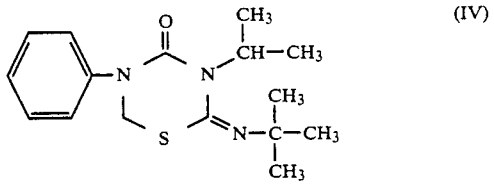

has been put to pracical use as an insecticide.

Japanese Laid-Open Patent Publication No. 140577/1986 discloses that tetrahydro-1,3,5-thiadiazin-4-ones in which the 2-imino group or at least one of the 3- and 5-positions is substituted by a certain substituted phenylalkyl group are novel compounds having insecticidal and acaricidal activities, and particularly, tetrahydro-1,3,5-thiadiazin-4-ones in which at least one of the 2-imino group and the 3-position is substituted by a substituted phenylalkyl group have marked insecticidal and acaricidal activities over the known compound Buprofezin. These insecticidal and acaricidal compounds, however, have no sufficient insecticidal activity on lepidopterous pests although they do have insecticidal activity on hemipterous and coleopterous pests. It has been desired therefore to develop a novel agent having similar activity to these insecticidal and acaricidal compounds and outstanding insecticidal and acaricidal activities on lepidopterous pests as well.

It is an object of this invention to provide an excellent insecticidal and acaricidal compound having a new structure, a broad insecticidal specrum and high insecticidal and acaricidal activities and being free from the problems of the prior art, an insecticidal and acaricidal agent, and a simple process for producing the insecticidal compound.

The present inventors made extensive investigations on tetrahydro-1,3,5-thiadiazin-4-ones in order to achieve the above object, and have now found that 2-(2,2,2-trifluoroethylimino)-tetrahydro-1,3,5-thiadiazin-4-ones or salts thereof have a broad insecticidal spectrum and exhibit high insecticidal and acaricidal activities also on lepidopterous pests on which known analogous compounds do not show sufficient insecticidal activity.

According to this invention, there is provided a tetrahydro-1,3,5-thiadiazin-4-one represented by the following general formula (I)

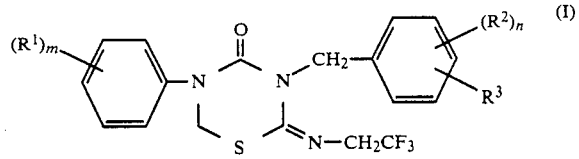

wherein each of $R^1$ and $R^2$ represents a halogen atom or an alkyl group having 1 to 4 carbon atoms; $R^3$ represents a halogen atom, an alkyl group having 1 to 4 carbon atoms, a cycloalkyl group having 3 to 6 carbon atoms, an alkoxy group having 1 to 4 carbon atoms, an acetyl group, a phenoxy group, a halo-substituted phenoxy group, a benzyl group, a benzyloxy group, a phenylcarbonyl group, a haloalkyloxy group having 1 to 4 carbon atoms, a haloalkyloxymethyl group having 1 to 4 carbon atoms, a haloalkenyloxy group having 2 to 4 carbon atoms, a haloalkylthio group having 1 to 4 carbon atoms, a haloalkylthiomethyl group having 1 to 4 carbon atoms, a haloalkenylthio group having 2 to 4 carbon atoms, a haloalkyl group having 1 to 8 carbon atoms, a haloalkenyl group having 2 to 8 carbon atoms, a alkyloxycarbonyl group having 1 to 8 carbon atoms, a substituted phenoxycarbonyl group, or a substituted pyridyloxy group; m represents 0, 1, 2 or 3; and n represents 0, 1, 2 or 3, or their salts.

The invention also provides a process for producing the tetrahydro-1,3,5-thiadiazin-4-ones of general formula (I) or their salts, which comprises reacting a compound represented by the following general formula (II)

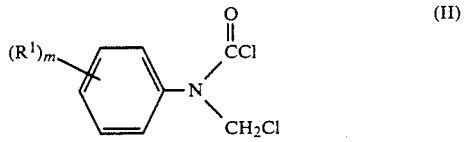

wherein $R^1$ and m are as defined above, with a compound represented by the following formula (III)

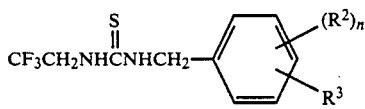

wherein R², R³ and n are as defined above.

The present invention further provides an insecticidal and acaricidal agent comprising at lest one tetrahydro-1,3,5-thiadiazin-4-one of general formula (I) or a salt thereof as active ingredient.

The tetrahydro-1,3,5-thiadiazin-4-ones of general formula (I) and their salts are not described in the literature, and are novel compounds.

When in the compound of this invention represented by general formula (I), the benzyl group at the 3-position of the thiadiazine ring has one substituent, it is preferably substituted at the 3- or 4-position, especially at the 4-position, of the benzyl group. When the benzyl group at the 3-position has two substituents, they are preferably substituted at the 3,4-positions of the benzyl 9roup. The 3-position substituent is preferably a halo9en atom, especially a fluorine or chlorine atom.

When the 4-position substituent is a halo9en atom, the halogen atom is preferably an iodine, chlorine, bromine or fluorine atom, especially the chlorine atom.

When the 4-position substituent is an alkyl group, the alkyl group is preferably a methyl, ethyl, isopropyl, n-butyl, sec-butyl or t-butyl group, especially the t-butyl group.

When the 4-position substituent is a cycloalkyl group, the cycloalkyl group is preferably a cyclopropyl, cyclopropylmethyl, cyclopentyl, or cyclohexyl group, especially the cyclohexyl group.

When the 4-position substituent is an alkoxy group, the alkoxy group is preferably a methoxy, ethoxy, isopropoxy, n-butoxy, sec-butoxy or t-butoxy group, especially the isopropoxy group.

When the 4-position substituent is a substituted phenoxy group, the substituted phenoxy group is preferably a 2-chlorophenoxy, 3-chlorophenoy, 4-chlorophenoxy, 2-fluorophenoxy, 3-fluorophenoxy, 4-fluorophenoxy, 2,4-dichlorophenoxy, 3,4-dichlorophenoxy, 3,5-dichlorophenoxy, 2,4-difluorophenoxy, 2,6-difluorophenoxy, 2-chloro-4-trifluoromethylphenoxy, 4-trifluoromethylphenoxy, 4-pentafluoroethylphenoxy, 4-trifluoromethoxyphenoxy, 4-methoxyphenoxy, 2-methylphenoxy, 3-methylphenoxy, 4-methylphenoxy, 2,4-dimethylphenoxy or 4-t-butylphenoxy group, especially the 2,4-dichlorophenoxy group.

When the 4-position substituent is a haloalkyloxy group, the halogen atom is preferably a bromine, chlorine or fluorine atom, especially the fluorine atom. Examples of preferred haloalkyloxy groups are difluoromethoxy, bromodifluoromethoxy, 2,2,2-trifluoroethoxy, 1,1,2,2-tetrafluoroethoxy, 2,2,3,3-tetrafluoropropyloxy and 2,2,3,3,4,4,4-hexafluorobutoxy groups. The trifluoromethoxy group is especially preferred.

When the 4-position substituent is a haloalkyloxymethyl group, the halogen atom is preferably a bromine, chlorine or fluorine atom, especially the fluorine atom. Preferred haloalkyloxymethyl groups include, for example, difluoromethoxymethyl, trifluoromethoxymethyl, chlorodifluoromethoxymethyl, bromodifluoromethoxymethyl, 2,2,2-trifluoroethoxymethyl, 1,1,2,2-tetrafluoroethoxymethyl and 2,2,2-trifluoro-1-methylethoxymethyl groups. The 2,2,2-trifluoroethoxymethyl group is preferred.

When the 4-position substituent is a haloalkenyloxy group, the halogen atom is preferably a bromine, chlorine or fluorine atom, especially the fluorine or chlorine atom. Examples of preferred haloalkenyloxy groups include 1,2,2-trichlorovinyloxy, 2,2-dichloro-1-fluorovinyloxy, 2-chloro-2-propeneoxy, 2-bromo-2-propeneoxy, 2,3-dichloro-2-propeneoxy, 3-chloro-2-n-buteneoxy and 3-chloro-3-buteneoxy groups. The 1,2,2-trichlorovinyloxy groups and 2-chloro-2-propeneoxy groups are especially preferred.

When the 4-position substituent is a haloalkylthio group, the halogen atom is preferably a bromine, chlorine or fluorine atom, especially preferably the fluorine atom. Examples of preferred haloalkylthio groups include difluoromethylthio, trifluoromethylthio, chlorodifluoromethylthio, bromodifluoromethylthio, 2,2,2-trifluoroethylthio, 1,1,2,2-tetrafluoroethylthio, 2,2,3,3-tetrafluoropropylthio and 2,2,3,3,4,4,4-hexafluorobutylthio groups. The trifluoromethylthio group is especially preferred.

When the 4-position substituent is a haloalkylthiomethyl group, the halogen atom is preferably a bromine, chlorine or fluorine atom. The fluorine atom is especially preferred. Examples of preferred haloalkylthiomethyl groups include difluoromethylthiomethyl, trifluoromethylthiomethyl, chlorodifluoromethylthiomethyl, bromodifluoromethylthiomethyl, 2,2,2-trifluoroethylthiomethyl, 1,1,2,2-tetrafluoroethylthiomethyl and 2,2,2-trifluoro-1-methylethylthiomethyl groups. The 2,2,2-trifluoroethylthiomethyl group is especially preferred.

When the 4-position substituent is a haloalkenylthio group, the halogen atom is preferably a bromine, chlorine or fluorine atom, especially a fluorine or chlorine atom. Examples of preferred haloalkenylthio groups include 1,2,2-trichlorovinylthio, 2,2-dichloro-1-fluorovinylthio, 2-chloro-2-propenethio, 2-bromo-2-propenethio, 2,3-dichloro-2-propenethio, 3-chloro-2-n-butenethio and 3-chloro-3-butenethio groups. The 1,2,2-trichlorovinylthio and 2-chloro-2-propenethio groups are preferred.

When the 4-position substituent is a haloalkyl group, the halogen atom is preferably a bromine, chlorine or fluorine atom, especially the fluorine atom. Preferred haloalkyl groups include, for example, chlorodifluoromethyl, chlorodibromomethyl, trichloromethyl, trifluoromethyl, pentafluoroethyl, n-heptafluoropropyl, n-tridecafluorohexyl, 2,2,2-trifluoroethyl and 2,2-bis-trifluoromethyl)-3,3,4,4,5,5,5-heptafluoropentyl groups. The pentafluoroethyl group is especially preferred.

When the 4-position substituent is an alkyloxycarbonyl group, its preferred examples include methoxycarbonyl, ethoxycarbonyl, n-propoxycarbonyl, isopropoxycarbonyl, n-butoxycarbonyl, isobutoxycarbonyl, sec-butoxycarbonyl, t-butoxycarbonyl, n-pentyloxycarbonyl, isopentyloxycarbonyl, n-hexyloxycarbonyl, 2-methylpentyloxycarbonyl, 3-methylpentyloxycarbonyl, n-heptyloxycarbonyl, t-heptyloxycarbonyl and n-octyloxycarbonyl groups. The t-butoxycarbonyl group is especially preferred.

When the 4-position substituent is a substituted phenoxycarbonyl group, examples of preferred substituted phenoxycarbonyl groups include phenoxycarbonyl, 2-chlorophenoxycarbonyl, 3-chlorophenoxycarbonyl, 4-chlorophenoxycarbonyl, 2-fluorophenoxycarbonyl, 3-fluorophenoxycarbonyl, 4-fluorophenoxycarbonyl, 2,4-dichlorophenoxycarbonyl, 3,4-dichlorophenoxycarbonyl, 3,5-dichlorophenoxycarbonyl, 2,4-difluorophenoxycarbonyl, 2,6-difluorophenoxycarbonyl, 4-trifluoromethylphenoxycarbonyl, 4-trifluoromethoxyphenoxycarbonyl, 4-methoxyphenoxycarbonyl, 2-methylphenoxycarbonyl, 3-methylphenoxycarbonyl, 4-methylphenoxycarbonyl, 2,4-dimethylphenoxycarbonyl and 4-t-butylphenoxycarbonyl groups. The 2,4-dichlorophenoxycarbonyl group is preferred.

When the 4-position substituent is a substituted pyridyloxy group, preferred examples of the substituted pyridyloxy group are 3-chloro-2-pyridyloxy, 3,5-dichloro-2-pyridyloxy, 5-trifluoromethyl-2-pyridyloxy and 3-chloro-5-trifluoromethyl-2-pyridyloxy groups. The 3-chloro-5-trifluoromethyl-pyridyloxy group is especially preferred.

When the phenyl group at the 5-position of the thiadiazine ring has one substituent, it may be a halogen atom, preferably a bromine, chlorine or fluorine atom, especially preferably the fluorine atom. The fluorine atom is preferably substituted at the 2-position. The substituent may also be an alkyl group which is preferably a methyl, ethyl, isopropyl or t-butyl group, the methyl group being especially preferred. The mthyl group is substituted preferably at the 3-position or the 4-position.

When the phenyl group at the 5-position has two substituents, they may be halogen atoms which are preferably bromine, chlorine and fluorine atoms; or alkyl groups which are preferably methyl, ethyl, isopropyl and t-butyl groups, the methyl group being especially preferred. The two substituents on the phenyl group are preferably at the 2,4-positions, 3,4-positions, or 2,6-positions. Preferably, the 2-position substituent is a fluorine atom; the 3-position substituent is a methyl group; the 4-position substituent is a methyl group; and the 6-position substituent is a fluorine atom.

When the phenyl group at the 5-position has three substituents, they may be halogen atoms which are preferably bromine, chlorine and fluorine atoms, the fluorine atom being especially preferred, and alkyl groups which are preferably methyl, ethyl, isopropyl and t-butyl groups, the methyl group being especially preferably. The three substituents on the phenyl group are preferably at the 2,4,6-postions or 3,4,6-positions. Preferably, the 2-position substituent is a fluorine atom; the 3-position substituent is a methyl group; the 4-position substituent is a methyl group; and the 6-position substituent is a fluorine atom.

Table 1 below shows typical examples of the compounds of the invention represented by general formula (I) without any intention of limiting the invention thereto.

TABLE 1

| Compound No. | $(R^1)_m$ | $(R^2)_n$ | $R^3$ |
|---|---|---|---|
| 1 | H | H | 4-CH$_3$ |
| 2 | H | H | 4-C$_2$H$_5$ |
| 3 | H | H | 4-CH(CH$_3$)$_2$ |
| 4 | H | H | 4-CH$_2$CH$_2$CH$_2$CH$_3$ |
| 5 | H | H | 4-CH(CH$_3$)CH$_2$CH$_3$ |
| 6 | H | H | 4-C(CH$_3$)$_3$ |
| 7 | 4-CH$_3$ | H | 4-CH$_3$ |
| 8 | 4-CH$_3$ | H | 4-C$_2$H$_5$ |
| 9 | 4-CH$_3$ | H | 4-CH(CH$_3$)$_2$ |
| 10 | 4-CH$_3$ | H | 4-CH$_2$CH$_2$CH$_2$CH$_3$ |
| 11 | 4-CH$_3$ | H | 4-CH(CH$_3$)CH$_2$CH$_3$ |
| 12 | 4-CH$_3$ | H | 4-C(CH$_3$)$_3$ |
| 13 | 2-F | H | 4-CH$_3$ |
| 14 | 2-F | H | 4-C$_2$H$_5$ |
| 15 | 2-F | H | 4-CH(CH$_3$)$_2$ |
| 16 | 2-F | H | 4-CH$_2$CH$_2$CH$_2$CH$_3$ |
| 17 | 2-F | H | 4-CH(CH$_3$)CH$_2$CH$_3$ |
| 18 | 2-F | H | 4-C(CH$_3$)$_3$ |
| 19 | 2-F, 4-CH$_3$ | H | 4-CH$_3$ |
| 20 | 2-F, 4-CH$_3$ | H | 4-CH(CH$_3$)$_2$ |
| 21 | 2-F, 4-CH$_3$ | H | 4-C(CH$_3$)$_3$ |
| 22 | 2-F, 6-F | H | 4-CH(CH$_3$)$_2$ |
| 23 | 2-F, 6-F | H | 4-C(CH$_3$)$_3$ |
| 24 | 2-F, 4-CH$_3$, 6-F | H | 4-CH(CH$_3$)$_2$ |
| 25 | 2-F, 4-CH$_3$, 6-F | H | 4-C(CH$_3$)$_3$ |
| 26 | 4-CH$_3$ | H | 4-OC$_2$H$_5$ |
| 27 | 4-CH$_3$ | H | 4-OCH(CH$_3$)$_2$ |
| 28 | 4-CH$_3$ | H | 4-OCH$_2$CH$_2$CH$_2$CH$_3$ |
| 29 | H | H | 4-Cl |
| 30 | H | H | 4-Br |
| 31 | 4-CH$_3$ | H | 4-Cl |
| 32 | 4-CH$_3$ | H | 4-Br |
| 33 | 2-F | H | 4-Cl |
| 34 | 2-F, 4-CH$_3$ | H | 4-Cl |
| 35 | H | 3-Cl | 4-Cl |
| 36 | 4-CH$_3$ | 3-Cl | 4-Cl |
| 37 | H | H | 4-CF$_3$ |
| 38 | 2-F | H | 4-CF$_3$ |
| 39 | 3-CH$_3$ | H | 4-CF$_3$ |
| 40 | 4-CH$_3$ | H | 4-CF$_3$ |
| 41 | 2-F, 4-CH$_3$ | H | 4-CF$_3$ |
| 42 | 2-F, 6-F | H | 4-CF$_3$ |
| 43 | H | H | 4-O—C$_6$H$_5$ |
| 44 | H | H | 4-O—(2,4-dichlorophenyl) |
| 45 | 4-CH$_3$ | H | 4-O—C$_6$H$_5$ |
| 46 | 2-F | H | 4-O—C$_6$H$_5$ |
| 47 | H | H | 4-OCH$_2$—C$_6$H$_5$ |
| 48 | 4-CH$_3$ | H | 4-OCH$_2$—C$_6$H$_5$ |
| 49 | 2-F | H | 4-OCH$_2$—C$_6$H$_5$ |
| 50 | H | H | 4-CH$_2$—C$_6$H$_5$ |

TABLE 1-continued

| Compound No. | $(R^1)_m$ | $(R^2)_n$ | $R^3$ |
|---|---|---|---|
| 51 | 4-CH₃ | H | 4-CH₂-(phenyl) |
| 52 | H | H | 4-C(=O)-(phenyl) |
| 53 | 4-CH₃ | H | 4-C(=O)-(phenyl) |
| 54 | 2-F | H | 4-C(=O)-(phenyl) |
| 55 | H | 3-F | 4-CF₃ |
| 56 | 4-CH₃ | 3-F | 4-CF₃ |
| 57 | 2-F | 3-F | 4-CF₃ |
| 58 | H | 3-F | 4-C(CH₃)₃ |
| 59 | 4-CH₃ | 3-F | 4-C(CH₃)₃ |
| 60 | 2-F | 3-F | 4-C(CH₃)₃ |
| 61 | H | 3-F | 4-O-(phenyl) |
| 62 | 4-CH₃ | 3-F | 4-O-(phenyl) |
| 63 | 2-F | 3-F | 4-O-(phenyl) |
| 64 | H | H | 4-C(=O)-CH₃ |
| 65 | 4-CH₃ | H | 4-C(=O)-CH₃ |
| 66 | H | H | 4-(cyclohexyl) |
| 67 | 4-CH₃ | H | 4-(cyclohexyl) |
| 68 | H | 3-CH₃ | 4-CH₃ |
| 69 | H | 3-Cl, 5-Cl | 4-CH₃ |
| 70 | H | H | 4-OCHF₂ |
| 71 | H | H | 4-OCF₃ |
| 72 | H | H | 4-OCClF₂ |
| 73 | H | H | 4-OCBrF₂ |
| 74 | H | H | 4-OCH₂CH₂F |
| 75 | H | H | 4-OCH₂CF₃ |
| 76 | H | H | 4-OCF₂CHF₂ |
| 77 | H | H | 4-OCH₂CF₂CHF₂ |
| 78 | H | H | 4-OCH₂CF₂CF₃ |
| 79 | H | H | 4-OCF₂CHFCF₃ |
| 80 | H | H | 4-CH₂OCBrF₂ |
| 81 | H | H | 4-CH₂OCH₂CF₃ |
| 82 | H | H | 4-OCCl=CCl₂ |
| 83 | H | H | 4-OCF=CHCl |
| 84 | H | H | 4-OCH₂CF=CH₂ |
| 85 | H | H | 4-OCH₂CCl=CH₂ |
| 86 | H | H | 4-OCH₂CBr=CH₂ |
| 87 | H | H | —OCH₂CCl=CHCl(Z) |
| 88 | H | H | —OCH₂CCl=CHCl(E) |
| 89 | H | H | 4-SCH₂F |
| 90 | H | H | 4-SCHF₂ |
| 91 | H | H | 4-SCF₃ |
| 92 | H | H | 4-SCBrF₂ |
| 93 | H | H | 4-SCClF₂ |
| 94 | H | H | —SC(CF₃)₂CF₂CF₂CF₃ |
| 95 | H | H | 4-CH₂SCH₂CF₃ |
| 96 | H | H | 4-SCH₂CCl=CH₂ |
| 97 | H | H | 4-CH₂CF₃ |
| 98 | H | H | 4-CF₂CF₃ |
| 99 | H | H | 4-CF₂CF₂CF₃ |
| 100 | H | H | 4-CF(CF₃)₂ |
| 101 | H | H | 4-CF₂(CF₂)₄CF₃ |
| 102 | H | H | 4-CH₂C(CF₃)₂CF₂CF₂CF₃ |
| 103 | H | H | 4-CH=CF₂ |
| 104 | H | H | 4-CH=CCl₂ |
| 105 | H | H | 4-CH=CBr₂ |
| 106 | H | H | 4-CH=CClF |
| 107 | H | H | 4-CH=CBrF |
| 108 | H | H | 4-CH=CBrCl |
| 109 | H | H | 4-CF=CF₂ |
| 110 | H | H | 4-CCl=CCl₂ |
| 111 | H | H | 4-CBr=CBr₂ |
| 112 | H | H | 4-CH=CClCF₃ |
| 113 | H | H | 4-CCH₃=CF₂ |
| 114 | H | H | 4-CCH₃=CCl₂ |
| 115 | H | H | 4-CCH₃=CBr₂ |
| 116 | H | H | 4-CH₂CF=CH₂ |
| 117 | H | H | 4-CH₂CCl=CH₂ |
| 118 | H | H | 4-CH₂CBr=CH₂ |
| 119 | H | H | 4-COOCH(CH₃)₂ |
| 120 | H | H | 4-COOC(CH₃)₃ |
| 121 | H | H | 4-COOCH₂(CH₂)₃CH₃ |
| 122 | H | H | 4-COOCH₂(CH₂)₆CH₃ |
| 123 | H | H | 4-COO—Q¹ |
| 124 | H | H | 4-COO—Q² |
| 125 | H | H | 4-Q—Q³ |
| 126 | 3-CH₃ | H | 4-OCHF₂ |
| 127 | 3-CH₃ | H | 4-OCF₃ |
| 128 | 3-CH₃ | H | 4-OCBrF₂ |
| 129 | 3-CH₃ | H | 4-OCH₂CF₃ |
| 130 | 3-CH₃ | H | 4-OCF₂CHF₂ |
| 131 | 3-CH₃ | H | 4-OCH₂CF₂CHF₂ |
| 132 | 3-CH₃ | H | 4-OCH₂CF₂CF₃ |
| 133 | 3-CH₃ | H | 4-OCF₂CHFCF₃ |
| 134 | 3-CH₃ | H | 4-CH₂OCH₂CF₃ |
| 135 | 3-CH₃ | H | 4-OCCl=CCl₂ |
| 136 | 3-CH₃ | H | 4-OCF=CHCl |
| 137 | 3-CH₃ | H | 4-OCH₂CF=CH₂ |
| 138 | 3-CH₃ | H | 4-OCH₂CCl=CH₂ |
| 139 | 3-CH₃ | H | 4-OCH₂CBr=CH₂ |
| 140 | 3-CH₃ | H | 4-SCHF₂ |
| 141 | 3-CH₃ | H | 4-SCF₃ |
| 142 | 3-CH₃ | H | 4-SCBrF₂ |
| 143 | 3-CH₃ | H | 4-SCClF₂ |
| 144 | 3-CH₃ | H | 3-CH₂SCH₂CF₃ |
| 145 | 3-CH₃ | H | 4-CH₂CF₃ |
| 146 | 3-CH₃ | H | 4-CF₂CF₃ |
| 147 | 3-CH₃ | H | 4-CF₂CF₂CF₃ |
| 148 | 3-CH₃ | H | 4-CF(CF₃)₂ |
| 149 | 3-CH₃ | H | 4-CH=CF₂ |
| 150 | 3-CH₃ | H | 4-CH=CCl₂ |
| 151 | 3-CH₃ | H | 4-CH=CBr₂ |
| 152 | 3-CH₃ | H | 4-CH=CClF |
| 153 | 3-CH₃ | H | 4-CH=CBrF |
| 154 | 3-CH₃ | H | 4-CH=CBrCl |
| 155 | 3-CH₃ | H | 4-CF=CF₂ |
| 156 | 3-CH₃ | H | 4-CCl=CCl₂ |

TABLE 1-continued

| Compound No. | $(R^1)_m$ | $(R^2)_n$ | $R^3$ |
|---|---|---|---|
| 157 | 3-CH$_3$ | H | 4-CH=CClCF$_3$ |
| 158 | 3-CH$_3$ | H | 4-CCH$_3$=CF$_2$ |
| 159 | 3-CH$_3$ | H | 4-CCH$_3$=CCl$_2$ |
| 160 | 3-CH$_3$ | H | 4-CCH$_3$=CBr$_2$ |
| 161 | 3-CH$_3$ | H | 4-CH$_2$CF=CH$_2$ |
| 162 | 3-CH$_3$ | H | 4-CH$_2$CCl=CH$_2$ |
| 163 | 3-CH$_3$ | H | 4-CH$_2$CBr=CH$_2$ |
| 164 | 3-CH$_3$ | H | 4-COOC(CH$_3$)$_3$ |
| 165 | 4-CH$_3$ | H | 4-OCHF$_2$ |
| 166 | 4-CH$_3$ | H | 4-OCF$_3$ |
| 167 | 4-CH$_3$ | H | 4-OCClF$_2$ |
| 168 | 4-CH$_3$ | H | 4-OCBrF$_2$ |
| 169 | 4-CH$_3$ | H | 4-OCH$_2$CH$_2$F |
| 170 | 4-CH$_3$ | H | 4-OCH$_2$CF$_3$ |
| 171 | 4-CH$_3$ | H | 4-OCF$_2$CHF$_2$ |
| 172 | 4-CH$_3$ | H | 4-OCH$_2$CF$_2$CHF$_2$ |
| 173 | 4-CH$_3$ | H | 4-OCH$_2$CF$_2$CF$_3$ |
| 174 | 4-CH$_3$ | H | 4-OCF$_2$CHFCF$_3$ |
| 175 | 4-CH$_3$ | H | 4-OCH$_2$OCBrF$_2$ |
| 176 | 4-CH$_3$ | H | 4-CH$_2$OCH$_2$CF$_3$ |
| 177 | 4-CH$_3$ | H | 4-OCCl=CCl$_2$ |
| 178 | 4-CH$_3$ | H | 4-OCF=CHCl |
| 179 | 4-CH$_3$ | H | 4-OCH$_2$CF=CH$_2$ |
| 180 | 4-CH$_3$ | H | 4-OCH$_2$CCl=CH$_2$ |
| 181 | 4-CH$_3$ | H | 4-OCH$_2$CBr=CH$_2$ |
| 182 | 4-CH$_3$ | H | 4-OCH$_2$CCl=CHCl(Z) |
| 183 | 4-CH$_3$ | H | 4-OCH$_2$CCl=CHCl(E) |
| 184 | 4-CH$_3$ | H | 4-SCH$_2$F |
| 185 | 4-CH$_3$ | H | 4-SCHF$_2$ |
| 186 | 4-CH$_3$ | H | 4-SCF$_3$ |
| 187 | 4-CH$_3$ | H | 4-SCBrF$_2$ |
| 188 | 4-CH$_3$ | H | 4-SCClF$_2$ |
| 189 | 4-CH$_3$ | H | 4-SC(CF$_3$)$_2$CF$_2$CF$_2$CF$_3$ |
| 190 | 4-CH$_3$ | H | 4-CH$_2$SCH$_2$CF$_3$ |
| 191 | 4-CH$_3$ | H | 4-SCH$_2$CCl=CH$_2$ |
| 192 | 4-CH$_3$ | H | 4-CH$_2$CF$_3$ |
| 193 | 4-CH$_3$ | H | 4-CF$_2$CF$_3$ |
| 194 | 4-CH$_3$ | H | 4-CF$_2$CF$_2$CF$_3$ |
| 195 | 4-CH$_3$ | H | 4-CF(CF$_3$)$_2$ |
| 196 | 4-CH$_3$ | H | 4-CF$_2$(CF$_2$)$_4$CF$_3$ |
| 197 | 4-CH$_3$ | H | 4-CH$_2$C(CF$_3$)$_2$CF$_2$CF$_2$CF$_3$ |
| 198 | 4-CH$_3$ | H | 4-CH=CF$_2$ |
| 199 | 4-CH$_3$ | H | 4-CH=CCl$_2$ |
| 200 | 4-CH$_3$ | H | 4-CH=CBr$_2$ |
| 201 | 4-CH$_3$ | H | 4-CH=CClF |
| 202 | 4-CH$_3$ | H | 4-CH=CBrF |
| 203 | 4-CH$_3$ | H | 4-CH=CBrCl |
| 204 | 4-CH$_3$ | H | 4-CF=CF$_2$ |
| 205 | 4-CH$_3$ | H | 4-CCl=CCl$_2$ |
| 206 | 4-CH$_3$ | H | 4-CBr=CBr$_2$ |
| 207 | 4-CH$_3$ | H | 4-CH=CClCF$_3$ |
| 208 | 4-CH$_3$ | H | 4-CCH$_3$=CF$_2$ |
| 209 | 4-CH$_3$ | H | 4-CCH$_3$=CCl$_2$ |
| 210 | 4-CH$_3$ | H | 4-CCH$_3$=CBr$_2$ |
| 211 | 4-CH$_3$ | H | 4-CH$_2$CF=CH$_2$ |
| 212 | 4-CH$_3$ | H | 4-CH$_2$CCl=CH$_2$ |
| 213 | 4-CH$_3$ | H | 4-CH$_2$CBr=CH$_2$ |
| 214 | 4-CH$_3$ | H | 4-COOCH(CH$_3$)$_2$ |
| 215 | 4-CH$_3$ | H | 4-COOC(CH$_3$)$_3$ |
| 216 | 4-CH$_3$ | H | 4-COOCH$_2$(CH$_2$)$_3$CH$_3$ |
| 217 | 4-CH$_3$ | H | 4-COOCH$_2$(CH$_2$)$_6$CH$_3$ |
| 218 | 4-CH$_3$ | H | 4-COO—Q$^1$ |
| 219 | 4-CH$_3$ | H | 4-COO—Q$^2$ |
| 220 | 4-CH$_3$ | H | 4-Q—Q$^3$ |
| 221 | 2-F | H | 4-OCHF$_2$ |
| 222 | 2-F | H | 4-OCF$_3$ |
| 223 | 2-F | H | 4-OCBrF$_2$ |
| 224 | 2-F | H | 4-OCH$_2$CF$_3$ |
| 225 | 2-F | H | 4-OCF$_2$CHF$_2$ |
| 226 | 2-F | H | 4-CH$_2$OCH$_2$CF$_3$ |
| 227 | 2-F | H | 4-OCCl=CCl$_2$ |
| 228 | 2-F | H | 4-OCH$_2$CCl=CH$_2$ |
| 229 | 2-F | H | 4-SCF$_3$ |
| 230 | 2-F | H | 4-CF$_2$CF$_3$ |
| 231 | 2-F | H | 4-CH=CCl$_2$ |
| 232 | 2-F | H | 4-CH=CClF |
| 233 | 2-F | H | 4-CF=CF$_2$ |
| 234 | 2-F | H | 4-CCl=CCl$_2$ |
| 235 | 2-F | H | 4-CH$_2$CCl=CH$_2$ |
| 236 | 2-F | H | 4-COOC(CH$_3$)$_3$ |
| 237 | 2-F, 4-CH$_3$ | H | 4-OCF$_3$ |
| 238 | 2-F, 4-CH$_3$ | H | 4-OCH$_2$CF$_3$ |
| 239 | 2-F, 4-CH$_3$ | H | 4-OCCl=CCl$_2$ |
| 240 | 2-F, 4-CH$_3$ | H | 4-OCH$_2$CCl=CH$_2$ |
| 241 | 2-F, 4-CH$_3$ | H | 4-SCF$_3$ |
| 242 | 2-F, 4-CH$_3$ | H | 4-CF$_2$CF$_3$ |
| 243 | 2-F, 4-CH$_3$ | H | 4-CH=CCl$_2$ |
| 244 | 2-F, 4-CH$_3$ | H | 4-COOC(CH$_3$)$_3$ |
| 245 | 2-F, 6-F | H | 4-OCF$_3$ |
| 246 | 2-F, 6-F | H | 4-OCH$_2$CF$_3$ |
| 247 | 2-F, 6-F | H | 4-OCCl=CCl$_2$ |
| 248 | 2-F, 6-F | H | 4-OCH$_2$CCl=CH$_2$ |
| 249 | 2-F, 6-F | H | 4-SCF$_2$ |
| 250 | 2-F, 6-F | H | 4-CF$_2$CF$_3$ |
| 251 | 2-F, 6-F | H | 4-CH=CCl$_2$ |
| 252 | 2-F, 6-F | H | 4-COOC(CH$_3$)$_3$ |
| 253 | 2-F, 4-CH$_3$, 6-F | H | 4-OCF$_3$ |
| 254 | 2-F, 4-CH$_3$, 6-F | H | 4-SCF$_3$ |
| 255 | 2-F, 4-CH$_3$, 6-F | H | 4-CF$_2$CF$_3$ |
| 256 | H | 3-F | 4-OCHF$_2$ |
| 257 | H | 3-F | 4-OCF$_3$ |
| 258 | H | 3-F | 4-OCH$_2$CF$_3$ |
| 259 | H | 3-F | 4-OCH$_2$CF$_2$CF$_3$ |
| 260 | H | 3-F | 4-OCH$_2$CF=CH$_2$ |
| 261 | H | 3-F | 4-OCH$_2$CCl=CH$_2$ |
| 262 | H | 3-F | 4-OCH$_2$CBr=CH$_2$ |
| 263 | H | 3-F | 4-SCF$_3$ |
| 264 | H | 3-F | 4-CF$_2$CF$_3$ |
| 265 | H | 3-F | 4-CH$_2$CCl=CH$_2$ |
| 266 | H | 3-Cl | 4-OCF$_3$ |
| 267 | H | 3-Cl | 4-OCH$_2$CF$_3$ |
| 268 | H | 3-Cl | 4-OCH$_2$CF$_2$CF$_3$ |
| 269 | H | 3-Cl | 4-OCH$_2$CF=CH$_2$ |
| 270 | H | 3-Cl | 4-OCH$_2$CCl=CH$_2$ |
| 271 | H | 3-Cl | 4-OCH$_2$CBr=CH$_2$ |
| 272 | H | 3-Cl | 4-SCF$_3$ |
| 273 | H | 3-Cl | 4-CF$_2$CF$_3$ |
| 274 | H | 3-Cl | 4-CH$_2$CCl=CH$_2$ |
| 275 | H | 3-Cl, 5-Cl | 4-OCH$_2$CF$_3$ |
| 276 | H | 3-Cl, 5-Cl | 4-OCH$_2$CF$_2$CF$_3$ |
| 277 | H | 3-Cl, 5-Cl | 4-OCH$_2$CF=CH$_2$ |
| 278 | H | 3-Cl, 5-Cl | 4-OCH$_2$CCl=CH$_2$ |
| 279 | 4-CH$_3$ | 3-F | 4-OCHF$_2$ |
| 280 | 4-CH$_3$ | 3-F | 4-OCF$_3$ |
| 281 | 4-CH$_3$ | 3-F | 4-OCH$_2$CF$_3$ |
| 282 | 4-CH$_3$ | 3-F | 4-OCH$_2$CF$_2$CF$_3$ |
| 283 | 4-CH$_3$ | 3-F | 4-OCH$_2$CF=CH$_2$ |
| 284 | 4-CH$_3$ | 3-F | 4-OCH$_2$CCl=CH$_2$ |
| 285 | 4-CH$_3$ | 3-F | 4-OCH$_2$CBr=CH$_2$ |
| 286 | 4-CH$_3$ | 3-F | 4-SCF$_3$ |
| 287 | 4-CH$_3$ | 3-F | 4-CF$_2$CF$_3$ |
| 288 | 4-CH$_3$ | 3-Cl | 4-OCF$_3$ |
| 289 | 4-CH$_3$ | 3-Cl | 4-OCH$_2$CF$_3$ |
| 290 | 4-CH$_3$ | 3-Cl | 4-OCH$_2$CF$_2$CF$_3$ |
| 291 | 4-CH$_3$ | 3-Cl | 4-OCH$_2$CF=CH$_2$ |
| 292 | 4-CH$_3$ | 3-Cl | 4-OCH$_2$CCl=CH$_2$ |
| 293 | 4-CH$_3$ | 3-Cl | 4-OCH$_2$CBr=CH$_2$ |
| 294 | 4-CH$_3$ | 3-Cl | 4-SCF$_3$ |
| 295 | 4-CH$_3$ | 3-Cl | 4-CF$_2$CF$_3$ |
| 296 | 4-CH$_3$ | 3-Cl | 4-CH$_2$CCl=CH$_2$ |
| 297 | 4-CH$_3$ | 3-Cl, 5-Cl | 4-OCH$_2$CF$_3$ |
| 298 | 4-CH$_3$ | 3-Cl, 5-Cl | 4-OCH$_2$CF$_2$CF$_3$ |
| 299 | 4-CH$_3$ | 3-Cl, 5-Cl | 4-OCH$_2$CF=CH$_2$ |
| 300 | 4-CH$_3$ | 3-Cl, 5-Cl | 4-OCH$_2$CCl=CH$_2$ |
| 301 | 2-F | 3-F | 4-OCH$_2$CF$_3$ |
| 302 | 2-F | 3-F | 4-OCH$_2$CF$_2$CF$_3$ |
| 303 | 2-F | 3-F | 4-OCH$_2$CF=CH$_2$ |
| 304 | 2-F | 3-F | 4-OCH$_2$CCl=CH$_2$ |
| 305 | 2-F | 3-F | 4-OCH$_2$CBr=CH$_2$ |
| 306 | 2-F | 3-F | 4-CF$_2$CF$_3$ |
| 307 | 2-F | 3-Cl | 4-OCF$_3$ |
| 308 | 2-F | 3-Cl | 4-OCH$_2$CF$_3$ |
| 309 | 2-F | 3-Cl | 4-OCH$_2$CF$_3$ |
| 310 | 2-F | 3-Cl | 4-OCH$_2$CF=CH$_2$ |
| 311 | 2-F | 3-Cl | 4-OCH$_2$CCl=CH$_2$ |
| 312 | 2-F | 3-Cl | 4-OCH$_2$CBr=CH$_2$ |
| 313 | 2-F | 3-Cl | 4-SCF$_3$ |
| 314 | 2-F | 3-Cl | 4-CF$_2$CF$_3$ |

TABLE 1-continued

| Compound No. | $(R^1)_m$ | $(R^2)_n$ | $R^3$ |
|---|---|---|---|
| 315 | 2-F | 3-Cl | 4-CH$_2$CCl=CH$_2$ |
| 316 | 2-F | 3-Cl, 5-Cl | 4-OCH$_2$CF$_3$ |
| 317 | 2-F | 3-Cl, 5-Cl | 4-OCH$_2$CF$_2$CF$_3$ |
| 318 | 2-F | 3-Cl, 5-Cl | 4-OCH$_2$CF=CH$_2$ |
| 319 | 2-F | 3-Cl, 5-Cl | 4-OCH$_2$CCl=CH$_2$ |
| 320 | 2-F, 4-CH$_3$ | 3-F | 4-OCH$_2$CF$_3$ |
| 321 | 2-F, 4-CH$_3$ | 3-F | 4-OCH$_2$CF$_2$CF$_3$ |
| 322 | 2-F, 4-CH$_3$ | 3-F | 4-OCH$_2$CF=CH$_2$ |
| 323 | 2-F, 4-CH$_3$ | 3-F | 4-OCH$_2$CCl=CH$_2$ |
| 324 | 2-F, 4-CH$_3$ | 3-F | 4-OCH$_2$CF$_3$ |
| 325 | 2-F, 4-CH$_3$ | 3-F | 4-OCH$_2$CCl=CH$_2$ |
| 326 | 2-F, 4-CH$_3$ | 3-F | 4-OCH$_2$CBr=CH$_2$ |
| 327 | 2-F, 4-CH$_3$ | 3-F | 4-CF$_2$CF$_3$ |
| 328 | 2-F, 4-CH$_3$ | 3-Cl | 4-OCF$_3$ |
| 329 | 2-F, 4-CH$_3$ | 3-Cl | 4-OCH$_2$CF$_3$ |
| 330 | 2-F, 4-CH$_3$ | 3-Cl | 4-OCH$_2$CF$_2$CF$_3$ |
| 331 | 2-F, 4-CH$_3$ | 3-Cl | 4-OCH$_2$CF=CH$_2$ |
| 332 | 2-F, 4-CH$_3$ | 3-Cl | 4-OCH$_2$CCl=CH$_2$ |
| 333 | 2-F, 4-CH$_3$ | 3-Cl | 4-OCH$_2$CBr=CH$_2$ |
| 334 | 2-F, 4-CH$_3$ | 3-Cl | 4-SCF$_3$ |
| 335 | 2-F, 4-CH$_3$ | 3-Cl | 4-CF$_2$CF$_3$ |
| 336 | 2-F, 4-CH$_3$ | 3-Cl | 4-CH$_2$CCl=CH$_2$ |
| 337 | 2-F, 4-CH$_3$ | 3-Cl, 5-Cl | 4-OCH$_2$CF$_3$ |
| 338 | 2-F, 4-CH$_3$ | 3-Cl, 5-Cl | 4-OCH$_2$CF$_2$CF$_3$ |
| 339 | 2-F, 4-CH$_3$ | 3-Cl, 5-Cl | 4-OCH$_2$CF=CH$_2$ |
| 340 | 2-F, 4-CH$_3$ | 3-Cl, 5-Cl | 4-OCH$_2$CCl=CH$_2$ |
| 341 | 2-F, 6-F | 3-F | 4-OCH$_2$CF$_3$ |
| 342 | 2-F, 6-F | 3-F | 4-OCH$_2$CCl=CH$_2$ |
| 343 | 2-F, 6-F | 3-F | 4-OCH$_2$CBr=CH$_2$ |
| 344 | 2-F, 6-F | 3-F | 4-CF$_2$CF$_3$ |
| 345 | 2-F, 6-F | 3-Cl | 4-OCF$_3$ |
| 346 | 2-F, 6-F | 3-Cl | 4-OCH$_2$CF$_3$ |
| 347 | 2-F, 6-F | 3-Cl | 4-OCH$_2$CCl=CH$_2$ |
| 348 | 2-F, 6-F | 3-Cl | 4-OCH$_2$CBr=CH$_2$ |
| 349 | 2-F, 6-F | 3-Cl | 4-CF$_2$CF$_3$ |
| 350 | 2-F, 6-F | 3-Cl | 4-OCH$_2$CCl=CH$_2$ |
| 351 | 2-F, 6-F | 3-Cl, 5-Cl | 4-OCH$_2$CF$_3$ |
| 352 | 2-F, 6-F | 3-Cl, 5-Cl | 4-OCH$_2$CF$_2$CF$_3$ |
| 353 | 2-F, 6-F | 3-Cl, 5-Cl | 4-OCH$_2$CF=CH$_2$ |
| 354 | 2-F, 6-F | 3-Cl, 5-Cl | 4-OCH$_2$CCl=CH$_2$ |
| 355 | 2-F, 4-CH$_3$, 6-F | 3-F | 4-OCH$_2$CF$_3$ |
| 356 | 2-F, 4-CH$_3$, 6-F | 3-Cl | 4-OCH$_2$CCl=CH$_2$ |
| 357 | 2-F, 4-CH$_3$, 6-F | 3-Cl, 5-Cl | 4-OCH$_2$CF$_3$ |
| 358 | 4-C$_2$H$_5$ | H | 4-OCHF$_2$ |
| 359 | 4-C$_2$H$_5$ | H | 4-OCF$_3$ |
| 360 | 4-C$_2$H$_5$ | H | 4-OCH$_2$CF$_3$ |
| 361 | 4-C$_2$H$_5$ | H | 4-OCCl=CCl$_2$ |
| 362 | 4-C$_2$H$_5$ | H | 4-OCH$_2$CBr=CH$_2$ |
| 363 | 4-C$_2$H$_5$ | H | 4-SCF$_3$ |
| 364 | 4-C$_2$H$_5$ | H | 4-CF$_2$CF$_3$ |
| 365 | 4-C$_2$H$_5$ | H | 4-CH=CCl$_2$ |

$Q^1$, $Q^2$ and $Q^3$ in Table 1 show the following structural formulae.

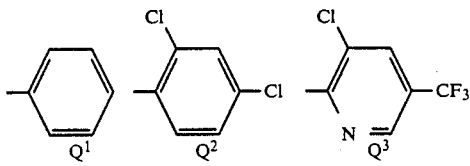

Examples of the salts of the compounds of general formula (I) include inorganic acid salts such as hydrochlorides, hydrobromides, hydroiodides, hydrofluorides, sulfates, hydrogen sulfates, nitrates, chlorates, perchlorates, phosphates, hydrogen phosphates, dihydrogen phosphates, thiocyanates and tetrafluoroborates; and organic acid salts such as formates, acetates, trichloroacetates, trifluoroacetates, citrates, lactates, oxalates, glycollates, malonates, succinates, malates, dodecylbenzenesulfonates, benzoates, salicylates and nicotinates.

The compounds of this invention represented by general formula (I) can be produced by the following

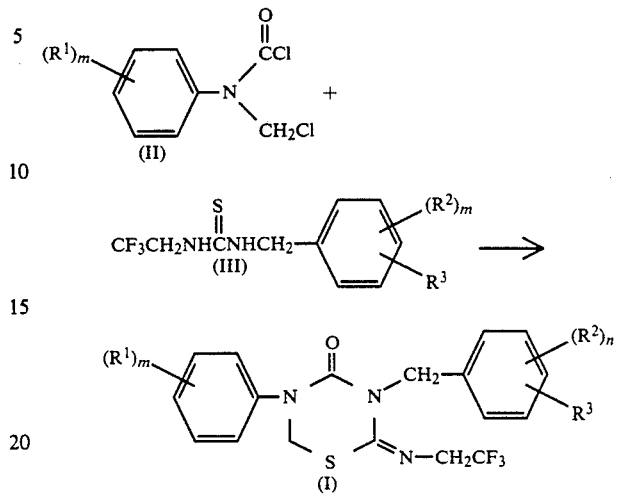

(In the formulae, $R^1$, $R^2$, $R^3$, m and n have the meanings defined hereinabove.)

The compounds of general formula (I) can be obtained by reacting the carbamoyl chloride derivative of general formula (II) with the thiourea derivative of general formula (III) in the absence or presence of a solvent, preferably in the presence of a solvent. Suitable solvents include, for example, acetone, methyl ethyl ketone, cyclohexanone, tetrahydrofuran, dioxane, ethyl ether, benzene, toluene, acetonitrile, ethanol, propanol, dichloromethane, chloroform, carbon tetrachloride, dimethylformamide, dimethylacetamide, dimethyl sulfoxide, 1,3-dimethyl-2-imidazolidinone, water and other solvents which do not affect the reaction.

The reaction is carried out under heating or in the presence of a base. In the case of performing the reaction under heating, the reaction temperature can be varied over a wide range depending upon the starting o, preferably 40 material. Generally, it is 30 to 250 C to 150° C. The reaction time is 0.1 to 30 hours, preferably 0.5 to 24 hours.

Suitable bases that may be used in performing the reaction include, for example, potassium hydroxide, sodium hydroxide, potassium carbonate, sodium carbonate, sodium hydrogen carbonate, triethylamine, pyridine, N,N-dimethylaniline, 1,8-diazabicyclo-5,4,0)-7-undecene. The reaction temperature and the reaction time may be varied over broad ranges depending upon the starting material. Generally, the reaction temperature is —10 to 200° C, preferably room temperature to 150° C, and the reaction time is 0.1 to 30 hours, preferably 0.5 to 24 hours.

In performing the above reaction, the carbamoyl chloride derivative of general formula (II) and the thiourea derivative of general formula (III) may be used in equimolar proportions, or one of them may be used in slight excess. In the case of carrying out the reaction using the base and obtaining the compound of general formula (I) in a free form, it is preferred to use the base in an amount of 2 moles per mole of the carbamoyl chloride derivative of general formula (II), or in a slightly excessive molar proportion with respect to the compound (II).

The starting carbamoyl chloride derivative of general formula (II) may be synthesized by a known method Journal of Organic Chemistry, vol. 39, page 2897 (1974)]. The thiourea of formula (III) may also be synthesized by a known method.

The salts of the compounds of the invention represented by general formula (I) can be produced by a known method. Specifically, the salts can be obtained by treating the compounds of general formula (I) with an inorganic acid such as hydrochloric acid, hydrobromic acid, hydroiodic acid, hydrofluoric acid, sulfuric acid, nitric acid, chloric acid, perchloric acid, phosphoric acid, thiocyanic acid and tetrafluoroboric acid, or an orgnaic acid such as formic acid, acetic acid, trichloroacetic acid, trifluoroacetic acid, citric acid, lactic acid, oxalic acid, glycollic acid, malonic acid, succinic acid, malic acid, dodecylbenzenesulfonic acid, benzoic acid, salicylic acid and nicotinic acid.

The compounds of the present invention represented by general formula (I) and their salts can be used to protect plants from many kinds of noxious arthropods encountered in various fields, for example in agriculture, forestry and horticulture.

For example, the compounds of formula (I) are effective against hemipterous insect pests such as small brown planthopper, brown planthopper, whitebacked planthopper, green rice leafhopper, zig-zag rice leafhopper, tea green leafhopper, jumping plantlice, westwood-greenhouse whitefly, citrus spiny whitefly, green peach aphid, cotton aphid, cabbage aphid, spiraea aphid, lace bug, bean bug, cletus punctiger Dallas, rice bug, whitespotted bug, southern green stink bug, arrowhead scale, San jose scale, and white peach scale; lepidopterous insect pests such as rice stem borer, rice leafroller, oriental corn borer, rice skipper, green rice caterpillar, apple leafminer, beet semi-looper, black cutworm, cutworm, summer fruit tortrix, apple leafroller, peach fruit moth, citrus leafminer, pear leafminer, cherry treeborer, gypsy moth, fall webworm, cabbage moth, rice armyworm, cabbage armyworm, tobacco cutworm and common cabbageworm; coleopterous insect pests such as cupreous chafer, soybean beetle, Japanese beetle, citrus flower chafer, rice water weevil, rice plant weevil and sugarcane wireworm; dipterous insect pests such as rice crane fly, soybean pod gall midge, melon fly, oriental fruit fly, rice leafminer, stone leek leafminer, bryony leafminer, onion maggot and seedcorn maggot; and thrips such as yellow tea thrips, *Thrips palmi* Karny and onion thrips; and mites such as two-spotted spider mite, Kanzawa spider mite, carmine spider mite, citrus red mite, fruittree red spider spider mite, hawthorn spider mite and broad mite.

They are also effective against pests which cause various damages to man and domestic animals, for example, the transmission of epidemics, blood sucking, stinging and biting and skin inflammation, such as house mosquito, *Culex pipiens molestus, Culex tritaeniorhyncus, Aedes albopictus,* house flies, *Boettcherisca pereqrina* Robineau-Desvoidy, *Calliphora lata* Coquillett, *Phormia regina* Meigen, *Drosophila melanogaster,* American cockroach, German cockroach, smokybrown cockroach, *Periplaneta brunnea* Burmeister, Japanese cockroach, *Ornithonyssus bacoti* Hirst, human louse, *Pediculus humanus humanus* De Geer, *Climex lectularus* Linne, human flea, dog flea, cat flea, oriental tussock moth, tea tussock moth, *Scolopendra subspinipes japonica,* rove beetle, and *Xanthochroa waterhousei* Harold; pests which damage foods or stored grains, such as mold mite, bread beetle, confused flour beetle, maize weevil, azuki bean weevil, common hide beetle and Indian meal moth; pests which damages furniture, building materials, books and apparel such as *Reticulitermes speratus* Kolbe, Formosan subterranean termite, powderpost beetle, *Gastrallus immarginatus* Mullerr, casemaking clothes moth and black carpet beetle; and so-called "unpleasant pests", such as *Telmatoscopus albipunctatus* Williston, *Chironomus plumosus* Linnaeus, midges, camel crickets, brown marmorated stink bug, *Thereuronema hilgendorfi* Verhoeff, *Oxidus gracilis* C. L. Koch, pillbug and Porcellio scaber Latreille.

The compounds of this invention show much higher insecticidal activity on lepidopterous insect pests than known compounds.

In actual application, the compound of the invention may be used singly without other components, but to make it easy to use as a control agent, it is generally applied as a mixture with a carrier. Formulation of the compound of the invention requires no particular conditions, and it may be prepared in any desired form such as an emulsifiable concentrate, a wettable powder, a dust, granules, a pulverulent agent, an oil, an aerosol, a fumigant or a bait by methods well known to those skilled in the art in accordance with the formulation of general agricultural chemicals.

The carrier, as used herein, denotes a synthetic or natural inorganic or organic material which is incorporated in order to aid in the arrival of the active ingredient at a site to be treated or facilitate storage, transportation and handling of the active ingredient compound.

Suitable solid carriers include, for example, clays such as montmorillonite and kaolinite; inorganic materials such as diatomaceous earth, terra alba, talc, vermiculite, gypsum, calcium carbonate, silica gel and ammonium sulfate, organic plant materials such as soybean meal, sawdust and wheat flour; and urea.

Suitable liquid carriers include, for example, aromatic hydrocarbons such as toluene, xylene and cumene, paraffinic hydrocarbons such as kerosene and mineral oils, halogenated hydrocarbons such as carbon tetrachloride, chloroform and dichloroethane, ketones such as acetone and methyl ethyl ketone, ethers such as dioxane and tetrahydrofuran, alcohols such as methanol, ethanol, propanol and ethylene glycol, dimethylformamide, dimethyl sulfoxide, and water.

To enhance the efficacy of the compounds of this invention, various adjuvants, either singly or in combination, may be combined with the compounds of the invention according to the formulation of the compounds, the situation in which they are applied, etc.

For the purpose of emulsification, dispersion, spreading, wetting, binding and stabilization, there may be used anionic surface-active agents such as lignosulfonates, alkylbenzenesulfonates and alkylsulfates; nonionic surface-active agents such as polyoxyalkylene alkyl ethers, polyoxyalkylene alkyl aryl ethers, polyoxyalkylene alkylamines, polyoxyalkylene alkylamides, polyoxyalkylene alkyl thioethers, polyoxyalkylene fatty acid esters, glycerin fatty acid esters, sorbitan fatty acid esters, polyoxyalkylene sorbitan fatty acid esters and polyoxypropylene polyoxyethylene block polymers; lubricants such as calcium stearate and waxes; stabilizers such as isopropyl hydrogen phosphate; and methyl cellulose, carboxymethyl cellulose, casein and gum arabic. These examples, however, are not limitative.

Better insecticidal and acaricidal activities may be obtained by using two or more compounds of this invention in combination. Furthermore, multipurpose compositions having a better efficacy may be prepared by mixing the compounds of the invention with other insecticides or acaricides, fungicides, nematocides, herbicides, plant growth regulating agents, fertilizers, machine oils and other agricultural chemicals. Synergistic effects can be expected from such compositions. Examples of the other insecticides or acaricides include fenthion, fenitrotion, diazinon, chlorpyrifos, chlorpyrifosmethyl, methidathion, dichlorvos, thiometon, acephate, trichlorphon, isoxathion, pyridafenthion, salithion, prothiofos, propaphos, EPN, sulprofos, NAC, MTMC, MIPC, BPMC, PHC, MPMC, XMC, pirimicarb, carbosulfan, benfuracarb, methomyl, oxamyl, pyrethrin, tetramethrin, phthalthrin, vaporthrin, allethrin, resmethrin, fenvalerate, esfenvalerate, permethrin, cypermethrin, fluvalinate, ethofenprox, flucythrinate, cyhalothrin, bifenthrin, diflubenzuron, chlorfluazuron, teflubenzuron, flufenoxuron, cypromazine, buprofezin, fenoxycarb, benzoepin, nereistoxin, bensultap, thiocyclam, avermectin, dicofol, amitraz, polynactins, fenbutatin oxide, cyhexatin, hexythiazox, flubenzamine, triarathene, clofentezine and milbemycin.

The compounds of this invention are stable to light, heat and oxidation. If required, however, suitable amounts of stabilizers, for example antioxidants or ultraviolet absorbers such as phenol derivatives [e.g., BHT (2,6-di-t-butyl-4-methylphenol) and BHA (butylhydroxyanisole)), bisphenol derivatives, arylamines (e.g., phenyl-α-naphthylamine, phenyl-β-naphthylamine, or a condensate of phenetidine and acetone), and benzophenone compounds may be added. This can give a composition having a more stabilized efficacy.

In the insecticidal and acaricidal agent of this invention, 0.1 to 95 % by weight, preferably 0.3 to 50 % by weight, of the compound of formula (I) or its salt is included as an active ingredient. In applying the insecticidal and acaricidal agent of this invention, the active ingredient is desirably used in a concentration of 0.01 to 5000 ppm, preferably 0.1 to 1000 ppm. The rate of application per 10 a is generally 1 g to 300 g as the active ingredient.

Contemplated equivalents of the compounds of this invention are those otherwise corresponding to formula (I) having one or more additional simple substituents on the benzyl and/or phenyl rings thereof, e.g , a substituent having one of the values of $R^3$, or a variation of the $R^3$ substituent, an alkyl group other than an alkyl having 1 to 4 carbon atoms, e.g., octyl, a substituted or fused ring cycloalkyl group; an alkoxy group other than an alkoxy having 1 to 4 carbon atoms, e.g., 2,2-dimethyl-propanoxy, n-octylox; an alkanoyl group other than acetyl, e.g., propanoyl or higher alkanoyl; an aryloxy group other than halo-substituted phenoxy, e.g., naphthoxy or biphenyloxy; an arylcarbonyl group other than phenylcarbonyl, e.g., ring substituted benzoyl; a haloalkyloxy group other than a haloalkyloxy having 1 to 4 carbon atoms, e.g., a halocycloalkyloxy group; a haloalkyloxyalkyl group other than a haloalkyloxymethyl having 1 to 4 carbon atoms, e.g., a halocycloalkyloxymethyl group, a haloalkyloxyethyl group; a haloalkynyloxy group other than a haloalkenyloxy having 2 to 4 carbon atoms, e.g., 3-trifluoromethyl-1-propynyloxy; a haloalkylthio group other than a haloalkylthio having 1 to 4 carbon atoms, e.g., a halocycloalkylthio group; a haloalkylthiomethyl group other than a haloalkylthiomethyl having 1 to 4 carbon atoms, e.g., a halocycloalkylthiomethyl group, a haloalkylthioethyl group; a haloalkynylthio group other than a haloalkenylthio having 2 to 4 carbon atoms, e.g., 3-trifluoromethyl-1-propynylthio; a haloalkyl group other than a haloalkyl having 2 to 4 carbon atoms, e.g., a halocycloalkyl group; a haloalkynyl group other than a haloalkenyl having 2 to 4 carbon atoms, e.g., 3-trifluoromethyl-1-propynyl; an alkenyloxycarbonyl group or an alkynyloxycarbonyl group other than alkyloxycarbonyl having 1 to 8 carbon atoms, e.g., allyloxycarbonyl, propargyloxycarbonyl; ring substituted pyrazoloxy, ring substituted pyrimidinoxy, ring substituted pyridazinoxy, ring substituted pyrazinoxy or ring substituted triazinoxy other than ring substituted pyridinoxy.

The following examples illustrate the present invention more specifically.

EXAMPLE 1

Synthesis of 2-(2,2,2-trifluoroethylimino)-3-(4-t-butylbenzyl)-5-phenyl-tetrahydro-1,3,5-thiadiazin-4-one (compound No. 6)

A solution of 0.65 g of trichloromethyl chloroformate in 10 ml of benzene was added dropwise to a solution of 0.69 g of 1,3,5-triphenyl-hexahydro-s-triazine in 20 ml of tetrahydrofuran with stirring at room temperature in a nitrogen stream. The solution was stirred at room temperature for 1.5 hours. Then, 2.00 g of 1-(4-t-butylbenzyl)-3-(2,2,2-trifluoroethyl)thiourea was added at room temperature with stirring, and subsequently, 6 ml of a 10 % aqueous solution of sodium hydroxide was added. The mixture was stirred at room temperature for 12 hours. Water (30 ml) was added to the reaction mixture, and it was extracted with 150 ml of ethyl acetate. The ethyl acetate solution was washed with water, and dried. Ethyl acetate was evaporated under reduced pressure. The resulting oily product was purified by column chromatography silica gel; eluent: hexane/ethyl acetate (10/1)) to give 0.42 g of the captioned compound.

Melting point: 113.0–114.0° C.

IR $\nu^{KBr}_{max}$(cm$^{-1}$) 2960, 1665, 1605, 1490, 1460, 1420, 1400, 1385, 1295, 1275, 1265, 1210, 1170, 1145, 1130, 1120, 1090, 950, 715.

$^1$H NMR $\delta^{CDCl_3}_{TMS}$ (ppm) 3(9H, s), 3.84(2H, q, J=9Hz), 4.87(2H, s), 5.32 (2H, s), 7.2–7.6(9H, m).

As an isomer, 0.37 g of 2-(4-t-butylbenzylimino)-3-(2,2,2-trifluoroethyl)-5-phenyl-tetrahydro-1,3,5-thiadiazin-4-one was obtained.

Melting point: 90.0–91.5° C.

IR $\nu^{KBr}_{max}$(cm$^{-1}$) 2960, 1670, 1610, 1490, 1450, 1390, 1365, 1335, 1260, 1200, 1160, 1120, 750.

$^1$NMR$\delta^{CDCl_3}_{TMS}$ (ppm): 4.57(2H, s) 4.92 (2H, s) 5.16(2H, q J=9Hz), 7.2–7.6(9H, m).

Synthesis of
2-(2,2,2-trifluoroethylimino)-3-(4-t-butylbenzyl)-5-(4-methylphenyl)-tetrahydro-1,3,5-thiadiazin-4-one (compound No. 12)

A solution of 1.42 g of trichloromethyl chloroformate in 20 ml of benzene was added dropwise to a solution of 1.72 g of 1,3,5-tris(4-methylphenyl)-hexahydro-s-triazine in 30 ml of tetrahydrofuran at room temperature with stirring in a nitrogen stream. The reaction solution was stirred at room temperature for 1 hour. Then, 4.0 g of 1-(4-t-butylbenzyl)-3-(2,2,2-trifluoroethyl)thiourea was added at room temperature with stirring, and subsequently 12 ml of a 10% aqueous solution of sodium hydroxide was added. The mixture was stirrerd at room temperature for 6 hours. Water (50 ml) was added to the reaction mixture, and it was extracted with 200 ml of ethyl acetate. The ethyl acetate layer was washed with water and dried, and ethyl acetate was evaporated under reduced pressure. The resulting oily product was purified by column chromatography [silica gel; eluent: hexane/ethyl acetate (10/1)) to give 0.79 g of the captioned compound.

Refractive index $n^{20}{}_D$: 1.5464. IR$\nu^{neat}{}_{max}$ (cm$^{-1}$) 2960, 1690, 1615, 1515, 1450, 1395, 1290, 1270, 1210, 1150, 1090, 940, 850, 825, 755, 725.

$^1$H NMR$\delta^{CDCl_3}$/TMS (ppm): 1.34(9H, s), 2.36(3H, s), 3.81 (2H, q, J=9Hz), 4.79(2H, s), 5.27(2H, s), 7.18–7.35(8H, m).

As an isomer, 1.29 g of 2-(4-t-butylbenzyl-imino)-3-(2,2,2-trifluoroethyl)-5-(4-methylphenyl)-tetrahydro-1,3,5-thiadiazin-4-one was obtained.

Refractive index $n^{20}{}_D$: 1.5537.

IR$\nu^{neat}{}_{max}$(cm$^{-1}$) 2960, 1700, 1620, 1515, 1450, 1395, 1335, 1305, 1270, 1210, 1160, 1120, 1080, 1045, 1020, 835, 820, 770.

$^1$ NMR $\delta^{CDCl_3}$/TMS (ppm): 1.36(9H, s), 2.36(3H, s), 4.52 (2H, s), 4.84(2H, s), 5.11(2H, q, J=9Hz), 7.18–7.41(8H. m).

EXAMPLE 3

Synthesis of
2-(2,2,2-trifluoroethylimino)-3-(4-trifluoromethylbenzyl)-5-phenyl-tetrahydro-1,3,5-thiadiazin-4-one
(compound No. 37)

A solution of 2.5 g of trichloromethyl chloroformate in 10 ml of benzene was added dropwise to a solution of 2.65 g of 1,3,5-triphenyl-hexahydro-s-triazine in 20 ml of tetrahydrofuran at room temperature with stirring in a nitrogen stream. The reaction solution was stirred at room temperature for 1.5 hours. Then, 4.00 g of 1-(4-trifluoromethylbenzyl)-3-(2,2,2-trifluoroethyl)thiourea was added at room temperature with stirring, and subsequently 15 ml of a 10 % aqueous solution of sodium hydroxide was added. The mixture was stirred at room temperature for 12 hours. Water (30 ml) was added to the reaction mixture, and it was extracted with 150 ml of ethyl acetate. The ethyl acetate solution was washed with water and dried. Under reduced pressure, ethyl acetate was evaporated. The resulting oily product was purified by column chromatography [slica gel; eluent: hexane/ethyl acetate (10/1)) to give 1.34 g of the captioned compound as a semisolid.

IR$\nu^{neat}{}_{max}$(cm$^{-1}$) 1680, 1615, 1500, 1450, 1390, 1330, 1270, 1140, 1125, 1065, 1015, 935, 840, 755.

$^1$H NMR$\delta^{CDCl_3}$/TMS (ppm): 3.80(2H, q, J=9Hz), 4.88(2H, s), 5.23(2H, s), 7.18–7.50(9H, m).

As an isomer, 0.76 g of 2-(4-trifluoromethyl-benzylimino)-3-(2,2,2-trifluoroethyl)-5-phenyl-tetra-hydro-1,3,5-thiadiazin-4-one was obtained.

Melting point: 127.0–128.0

IR $\nu^{KBr}{}_{max}$(cm$^{-1}$) 1695, 1625, 1500, 1455, 1400, 1325, 1280, 1160, 1120, 1070, 1025, 835, 825, 755.

$^1$H NMR $\delta^{CDCl_3}$/TMS (ppm) 4.60(2H, s), 4.90(2H, s), 5.11 (2H, q, J=9Hz), 7.26-7.44(9H, m).

EXAMPLE 4

Synthesis of
2-(2,2,2-trifluoroethylimino)-3-(4-trifluoromethylbenzyl)-5-(2-fluorophenyl)-tetrahydro-1,3,5-thiadiazin-4-one (compound No. 38)

A solution of 1.00 g of trichloromethyl chloroformate in 20 ml of benzene was added dropwise to a solution of 1.23 g of 1,3,5-tris(2-fluorophenyl)-hexahydro-s-triazine in 30 ml of tetrahydrofuran at room temperatue with stirring in a nitrogen stream. The reaction solution was stirred at room temperature for 1 hour. Then, 3.16 g of 1-(4-trifluoromethylbenzyl)-3-(2,2,2-trifluoroethyl)thiourea was added with stirring at room temperature, and subsequently, 1.5 ml of triethylamine was added. The mixture was stirred at room temperature for 6 hours. Water (50 ml) was added to the reaction mixture, and it was extracted with 200 ml of ethyl acetate. The ethyl acetate solution was washed with water and dried. Under reduced pressure, ethyl acetate was evaporated. The resulting oily product was purified by column chromatography silica gel; eluent: hexane/ethyl acetate (10/1)) to give 0.20 g of the captioned compound.

Refractive index $n^{20}{}_D$: 1.5225.

IR$\nu^{neat}{}_{max}$(cm$^{-1}$): 1690, 1620, 1505, 1450, 1400, 1330, 1290, 1275, 1265, 1260, 1240, 1150, 1130, 1090, 1070, 1020, 940, 845, 760.

$^1$H NMR$\delta^{CDCl_3}$/TMS (ppm): 3.72(2H, q, J=9Hz), 4.72 (2H, s), 5.29(2H, s), 7.00–7.50(4H, m), 7.51 (4H, s).

As an isomer, 0.30 g of 2-(4-trifluoromethyl-benzylimino)-3-(2,2,2-trifluoroethyl)-5-(2-fluorophenyl)-tetrahydro-1,3,5-thiadiazin-4-one was obtained.

Refractive index: $n^{20}{}_D$=1.5291.

IR $\nu^{neat}{}_{max}$(cm$^{-1}$) 1700, 1620, 1505, 1445, 1415, 1400, 1325, 1275, 1260, 1235, 1160, 1125, 1110, 1065, 1020, 830, 760.

$^1$H NMR $\delta^{CDCl_3}$/TMS (ppm) 4.52(2H, s), 4.77(2H, s), 5.11 (2H, q, J=10Hz), 6.90–7.70(8H, m).

EXAMPLE 5

Synthesis of
2-(2,2,2-trifluoroethylimino)-3-(4-trifluoromethylbenzyl)-5-(3-methylphenyl)-tetra-hydro-1,3,5-thiadiazin-4-one (compound No. 39)

A solution of 1.00 g of trichloromethyl chloroformate in 10 ml of benzene was added dropwise to a solution of 1.19 g of 1,3,5-tris(3-methylphenyl)-hexahydro-s-triazine in 20 ml of tetrahydrofuran at room temperature with stirring in a nitrogen stream. The reaction mixture was stirred at room temperature for 1.5 hours. Then, 3.16 g of 1-(4-trifluoromethylbenzyl)-3-(2,2,2-trifluoroethyl)thiourea was added at room temperature with stirring, and subsequently, 4.0 ml of triethylamine was added. The mixture was stirred at room temperature for 12 hours. Aqueous ammonia (30 ml) was added to the reaction mixture, and it was extracted with 150 ml of ethyl acetate. The ethyl acetate solution was washed with water and dried. Under reduced pressure, ethyl acetate was evaporated. The resulting oily product was purified by column chromatography silica gel; eluent: hexane/ethyl acetate (10/1)]to give 0.54 g of the captioned compound.

Refractive index $n^{20}{}_D$: 1.5340.

IR$\nu^{neat}{}_{max}$(cm$^{-1}$) 1680, 1610, 1490, 1445, 1380, 1315, 1265, 1255, 1105, 1065, 1045, 1025, 935.

$^1$H NMR $\delta^{CDCl_3}$/TMS (ppm): 2.40(3H, s), 3.82 (2H, q, J=9Hz), 4.86(2H, s), 5.36(2H, s), 7.00–7.50 (4H, m), 7.60(4H, s).

As an isomer, 0.31 g of 2-(4-trifluoromethyl-benzylimino)-3-(2,2,2-trifluoroethyl)-5-(3-methylphenyl)-tetrahydro-1,3,5-thiadiazin-4-one was obtained.

Melting point: 97.0–98.0° C.

IR$\nu^{neat}{}_{max}$(cm$^{-1}$) 1690, 1615, 1490, 1440, 1415, 1390, 1325, 1270, 1260, 1155, 1110, 1065, 1015.

$^1$H NMR $\delta^{CDCl_3}$/TMS (ppm) 2.39(3H, s), 4.57(2H, s), 4.88 (2H s), 5.15(2H, q, J=10Hz), 7.00–7.80(8H, m).

EXAMPLE 6

Synthesis of 2-(2,2,2-trifluoroethylimino)-3-(4-trifluoromethylbenzyl)-5-(4-methylphenyl)-tetrahydro-1,3,5-thiadiazin-4-one (compound No. 40):

1.00 g of N-chloromethyl-N-(4-methylphenyl)carbamoyl chloride and 1.45 g of 1-(4-trifluoromethylbenzyl)-3-(2,2,2-trifluoroethyl)thiourea were dissolved in 30 ml of benzene, and the solution was heated under reflux for 4 hours. After the reaction, benzene was evaporated under reduced pressure. The resulting oily product was purified by column chromatography [silica gel; eluent: hexane/ethyl acetate (10/1)] to give 1.27 g of the captioned compound.

Melting point: 62.0–63.0° C.

This product was washed with small amount of hexane and dried to give crystals having a melting point of 77.0–78.5° C.

IR$\nu^{KBr}_{max}$(cm$^{-1}$) 1675, 1610, 1510, 1440, 1390, 1325, 1285, 1265, 1205, 1135, 1105, 1060, 1015, 935, 840, 815, 740.

$^1$H NMR $\delta^{CDCl_3}$/TMS (ppm): 2.38(3H, s), 3.78(2H, q, J=9Hz), 4.80(2H, s), 5.35(2H, s), 7.23(4H, s), 7.57(4H, s).

As an isomer, 0.30 g of 2-(4-trifluoromethyl-benzylimino)-3-(2,2,2-trifluoroethyl)-5-(4-methylphenyl)-tetrahydro-1,3,5-thiadiazin-4-one was obtained.

Melting point: 97.0–98.5° C.

IR$\nu^{KBr}_{max}$ (cm$^{-1}$): 1675, 1590, 1505, 1440, 1405, 1390, 1410, 1405, 1390, 1315, 1295, 1260, 1150, 1105, 1060.

$^1$H NMR $\delta^{CDCl_3}$/TMS (ppm): 2.40(3H, s), 4.58(2H, s), 4.86 (2H, s), 5.15(2H, q, J=10Hz), 7.24(4H, s), 7.50(2H, d, J=8Hz), 7.65(2H, d, J=8Hz).

EXAMPLE 7

Synthesis of 2-(2,2,2-trifluoroethylimino)-3-(4-isopropyloxybenzyl)-5-(4-methylphenyl)-tetrahydro-1,3,5-thiadiazin-4-one (compound No. 27)

1.00 g of N-chloromethyl-N-(4-methylphenyl)carbamoyl chloride and 1.40 g of 1-(4-isopropyloxybenzyl)-3-(2,2,2-trifluoroethyl)thiourea were dissolved in 30 ml of benzene, and the solution was heated under reflux for 4 hours. After the reaction, benzene was evaporated under reduced pressure. The resulting oily product was purified by column chromatography silica gel; eluent: hexane/ethyl acetate (10/1)1 to give 0.75 g of the captioned compound.

Refractive index n$^{20}$D: 1.5462.

IR $\nu^{neat}_{max}$(cm$^{-1}$) 1690, 1610, 1510, 1445, 1380, 1260, 1240, 1135, 1080, 1035, 950, 935, 840, 815.

$^1$H NMR $\delta^{CDCl_3}$/TMS (ppm): 1.31(6H, d, J=6Hz), 2.36(3H, s), 3.81(2H, q, J=9Hz), 4.39–4.62(1H, m), 4.75 (2H, s), 5.26(2H, s), 6.80(2H, d, J=8Hz), 7.18(4H, s), 7.39(2H, d, J=8Hz).

As an isomer, 0.6 g of 2-(4-isopropyloxybenzylimino)-3-(2,2,2-trifluoroethyl)-5-(4-methylphenyl)-tetra-hydro-1,3,5-thiaziazin-4-one was obtained.

Melting point: 110.0–112.5° C.

IR$\nu^{neat}_{max}$(cm$^{-1}$) 1690, 1610, 1510, 1440, 1385, 1260, 1240, 1150, 1110, 1070, 1040, 1015, 950, 820.

$^1$H NMR $\delta^{CDCl_3}$/TMS (ppm): 1.36(6H, d, J=6Hz), 2.37(3H, s), 4.44(2H, s), 4.38–4.61(1H, m), 4.80(2H, s), 5.10(2H, q, J=10Hz), 6.86(2H, d, J=8Hz), 7.18 (4H, s), 7.23(2H, d, J=8Hz).

EXAMPLE 8

Synthesis of 2-(2,2,2-trifluoroethylimino)-3-(3,4-dichlorobenzyl)-5-phenyl-tetrahydro-1,3,5-thiadiazin-4-one (compound No. 35)

1.00 g of N-chloromethyl-N-phenylcarbamoyl chloride and 1.55 g of 1-(3,4-dichlorobenzyl)-3-(2,2,2-trifluoroethyl)thiourea were dissolved in 30 ml of benzene, and the solution was heated under reflux. After the reaction, benzene was evaporated under reduced pressure. The resulting oily product was purified by column chromatography silica gel; eluent: hexane/ethyl acetate (10/1)] to give 0.88 g of the captioned compound.

Melting point: 99.1–99.6° C.

IR$\nu^{KBr}_{max}$(cm$^{-1}$) 1675, 1665, 1610, 1390, 1285, 1265, 1135, 1120, 1085, 1030, 990, 930, 750, 720, 690.

$^1$H NMR $\delta$CDCl$_3$/TMS (ppm): 3.80(2H, q, J=9Hz), 4.88(2H, s), 5.20(2H, s), 7.27–7.61(8H, m).

As an isomer, 0.20 g of 2-(3,4-dichlorobenzylimino)-3-(2,2,2-trifluoroethyl)-5-phenyl-tetrahydro-1,3,5-thiadiazin-4-one was obtained as a semisolid.

IR $\nu^{neat}_{max}$(cm$^{-1}$) 1695, 1620, 1505, 1495, 1470, 1445, 1390, 1330, 1265, 1210, 1155, 1115, 1080, 1030, 835, 815, 760.

$^1$H NMR $\delta$CDCl$_3$/TMS (ppm): 4.48(2H, s), 4.90(2H, s), 5.08 (2H, q, J=10Hz), 7.10–7.41(8H, m).

EXAMPLE 9

Synthesis of 2-(2,2,2-trifluoroethylimino)-3(4-trifluoromethylbenzyl)-5-(2-fluoro-4-methylphenyl)-tetrahydro-1,3,5-thiadiazin-4-one (compound No. 41)

0.60 g of N-chloromethyl-N-(2-fluoro-4-methylphenyl)carbamoyl methylbenzyl)-3-(2,2,2-trifluoroethyl)thiourea were dissolved in 30 ml of toluene, and the solution was heated under reflux for 4 hours. After the reaction, toluene was evaporated under reduced pressure. The resulting oily product was purified by column chromatography silica gel; eluent: hexane/ethyl acetate (10/1)) to give 0.50 g of the captioned compound as a semisolid.

IR $\nu^{neat}_{max}$ (cm$^{-1}$): 1690, 1620, 1515, 1450, 1400, 1330, 1270, 1140, 1090, 1070, 1020, 940, 850, 825, 765, 750, 725, 710.

$^1$H NMR $\delta$CDCl$_3$/TMS (ppm): 2.35(3H, s), 3.78(2H, q, 8Hz), 4.74(2H, s), 5.30(2H, s), 6.96–7.33 (3H, m), 7.61(4H, s).

As an isomer, 0.17 g of 2-(4-trifluoro-methylbenzylimino)-3-(2,2,2-trifluoroethyl)-5-(2-fluoro-4-methylphenyl)-tetrahydro-1,3,5-thiadiazin-4-one was obtained.

Melting point: 115–116° C.

IR $\nu^{KBr}_{max}$(cm$^{-1}$) 1690, 1630, 1515, 1450, 1400, 1330, 1310, 1255, 1170, 1110, 1070, 1045, 1015, 945, 830, 825, 765, 745.

$^1$H NMR$\delta$CDCl$_3$/TMS (ppm) 2.36(3H, s), 4.55(2H, s), 4.77(2H, s), 5.10(2H, q, J=10Hz), 6.96–7.36 (3H, m), 7.50(2H, d, J=9Hz), 7.70(2H, d, J=9Hz).

EXAMPLE 10

Synthesis of 2-(2,2,2-trifluoroethylimino)-3-(4-phenoxybenzyl)-5-phenyl-tetrahydro-1,3,5-thiadiazin-one (compound No. 43)

1.00 g of N-chloromethyl-N-phenylcarbamoyl chloride and 1.67 g of 1-(4-phenoxybenzyl)-3-(2,2,2-trifluoroethyl)thiourea were dissolved in 30 ml of benzene, and the solution was heated under reflux for hours. After the reaction, benzene was evaporated under reduced pressure. The resulting oily product was purified by column chromatography [silica gel; eluent: solvent: hexane/ethyl acetate (10/1)] to give 0.87 g of the captioned compound.

Refractive index $n^{20}_D$: 1.5903.

IR $\nu^{neat}_{max}$ (cm$^{-1}$) 1680, 1610, 1590, 1500, 1490, 1445, 1390, 1285, 1270, 1265, 1230, 1205, 1165, $^1$H NMR $\delta$CDCl$_3$/TMS (ppm) 3.81(2H, q, J=8Hz), 4.81 (2H, s), 5.23(2H, s), 6.80-7.50(14H, m).

As an isomer, 0.15 g of 2-(4-phenoxybenzyl-imino)-3-(2,2,2-trifluoroethyl)-5-phenyl-tetrahydro1,3,5-thiadiazin-4-one was obtained.

Refractive index $n^{20}_D$: 1.5845

IR $\nu^{neat}_{max}$ (cm$^{-1}$) 1700, 1620, 1590, 1505, 1495, 1445, 1390, 1335, 1305, 1275, 1265, 1240, 1205, 1160, 1120.

$^1$H NMR $\delta$CDCl$_3$/TMS (ppm) 4.49(2H s) 4 85(2H s) 5.08(2H, q, J=9Hz), 6.80-7.60(14H, m).

EXAMPLE 11

Synthesis of 2-(2,2,2-trifluoroethylimino)-3-(4-trifluoromethoxybenzyl)-5-phenyl-tetrahydro-1,3,5-thiadiazin-4-one (compound No. 71)

0.61 g of N-chloromethyl-N-phenylcarbamoyl chloride and 1.00 g of 1-(4-trifluoromethoxybenzyl)-(2,2,2-trifluoroethyl)thiourea were dissolved in 30 ml of benzene, and the solution was heated under reflux for 4 hours. After the reaction, benzene was evaporated under reduced pressure. The resulting oily product was purified by column chromatography silica gel; developing solvent: hexane/ethyl acetate (10:1)) to give 0.68 g of the captioned compound.

Melting point: 54.0–56.0 ° C.

IR $\nu^{KBr}_{max}$ (cm$^{-1}$) 1675, 1665, 1610, 1500, 1450, 1395, 1260, 1140, 1120, 930, 840, 765.

$^1$H NMR $\delta$CDCl$_3$/TMS (ppm): 3.78(2H, q, J=9Hz), 4.84 (2H, s), 5.25(2H, s), 7.04-7.91(9H, m).

As an isomer, 0.17 g of 2-(4-trifluoromethoxy-benzylimino)-3-(2,2,2-trifluoroethyl)-5-phenyl-tetrahydro-1,3,5-thiadiazin-4-one was obtained.

Melting point: 84.0–87.0° C.

IR$\nu^{KBr}_{max}$ (cm$^{-1}$) 1690, 1615, 1505, 1495, 1440, 1390, 1260, 1170, 1120, 835, 820, 755.

$^1$H NMR $\delta$CDCl$_3$/ TMS (ppm) 4.52(2H, s), 4.69(2H, s), 5.09(2H, q, J=9Hz), 7.11-7.36(9H, m).

EXAMPLE 12

Synthesis of 2-(2,2,2-trifluoroethylimino)-3-(4-difluoromethoxybenzyl)-5-(4-methylphenyl)-tetrahydro-1,3,5-thiadiazin-4-one (compound No. 165)

0.69 g of N-chloromethyl-N-(4-methylphenyl)carbamoyl chloride and 1.00 g of 1-(4-difluoromethoxybenzyl)-3-(2,2,2-trifluoroethyl)thiourea were dissolved in 30 ml of toluene, and the solution was heated under reflux for 4 hours. After the reaction, toluene was evaporated under reduced pressure. The resulting oily product was purified by column chromatography silica gel; developing solvent hexane/ethyl acetate (10:1)]to give 0.80 g of the captioned compound.

Refractive index $n^{20}_D$: 1.5461.

IR $\nu^{neat}_{max}$ (cm$^{-1}$) 1680, 1620, 1515, 1450, 1400, 1270, 1130, 1090, 1045, 940, 850, 820, 755.

$^1$H NMR $\delta$CDCl$_3$/TMS (ppm): 2.33(3H, s), 3.75(2H, q, J=9Hz), 4.75(2H, s), 5.18(2H, s), 6.39(1H, t, J=74Hz), 6.90-7.44(8H, m).

As an isomer, 0.19 g of 2-(4-difluoromethoxybenzylimino)-3-(2,2,2-trifluoroethyl)-5-(4-methylphenyl)-tetrahydro-1,3,5-thiadiazin-4-one was obtained.

Melting point: 88.5–90.0° C.

IR $\nu^{KBr}_{max}$ (cm$^{-1}$) 10, 1685, 1620, 1520, 1445, 1390, 1265, 1175, 1120, 1050, 830.

$^1$H NMR $\delta$CDCl$_3$/TMS (ppm): 2.36(3H, s), 4.46(2H, s), 4.79(2H, s), 5.04(2H, q, J=9Hz), 6.33(1H, t, J=74Hz), 6.97-7.28(8H, m).

EXAMPLE 13

Synthesis of 2-(2,2,2-trifluoroethylimino)-3-(4-trifluoromethylthiobenzyl)-5-phenyl-tetrahydro-1,3,5-thiadiazin-4-one (compound No. 91)

A solution of 1.77 g of trichloromethyl chloroformate in 10 ml of benzene was added dropwise to a solution of 1.89 g of 1,3,5-triphenyl-hexahydro-striazine with stirring at room temperature under a nitrogen current. The reaction solution was stirred at room temperature for 1.5 hours. Then, 3.0 g of 1-(4-trifluoromethylthiobenzyl)-3-(2,2,2-trifluoroethyl)thiourea was added to the solution at room temperature with stirring, and subsequently, 1.5 ml of triethylamine was added. The mixture was stirred at room temperature for 12 hours. Aqueous ammonia (30 ml) was added to the reaction solution, and the mixture was extracted with 150 ml of ethyl acetate. The ethyl acetate solution was washed with water and dried, and ethyl acetate was evaporated under reduced pressure. The resulting oily product was purified by column chromatography silica gel; developing solvent hexane/ethyl acetate (10:1)) to give 0.47 g of the captioned compound.

Melting point: 89.5–90.0° C.

IR $\nu^{KBr}_{max}$ (cm$^{-1}$) 1660, 1605, 1500, 1490, 1430, 1395, 1285, 1270, 1215, 1140, 1120, 1085, 930, 840, 750, 715.

$^1$H NMR $\delta$CDCl$_3$/ TMS (ppm): 3.80(2H, q, J=9Hz), 4.84 (2H, s), 5.32(2H, s), 7.20-7.60(9H, m).

As an isomer, 0.11 g of 2-(4-trifluoromethylthiobenzylimino)-3-(2,2,2-trifluoroethyl)-5-phenyltetrahydro-1,3,5-thiadiazin-4-one was obtained as a semisolid.

IR $\nu^{KBr}_{max}$ (cm 1695, 1615, 1490, 1440, 1390, 1335 1255, 1170, 1150, 1120, 1080, 810, 755, 715.

$^1$H NM CDCl$_3$/ TMS (ppm): 4.28(2H, s), 4.78(2H, s), 5.01(2H, q, J=9Hz), 7.10-7.49(9H, m).

EXAMPLE 14

Synthesis of 2-(2,2,2-trifluoroethylimino)-3-(2,2,2-trifluoroethoxy)benzyl)-5-phenyl-tetrahydro-1,3,5-thiadiazin-4-one (compound No. 75)

A solution of 1.00 g of trichloromethyl chloroformate in 10 ml of benzene was added dropwise to a solution of 1.08 g of 1,3,5-triphenyl-hexahydro-s-triazine in 20 ml of tetrahydrofuran with stirring at room temperature under a nitrogen current. The reaction solution was stirred at room temperature for 1.5 hours, and then 3.46 g of 1-4-(2,2,2-trifluoroethoxy)benzyl]-3-(2,2,2-trifluoroethyl)thiourea was added at room temperature with stirring, and subsequently, 5.0 ml of triethylamine was added. The mixture was stirred at room temperature for 12 hours. Water (30 ml) was added to the reaction mixture, and the mixture was extracted with 150 ml of ethyl acetate. The ethyl acetate solution was washed with water and dried, and ethyl acetate was evaporated under reduced pressure. The resulting oily product was purified by column chromatography silica gel; developing solvent hexane/ethyl acetate (10:1)) to give 0.56 g of the captioned compound.

Refractive index $n^{20}_D$: 1.5324.

IR $\nu^{KBr}_{max}$(cm$^{-1}$) 1670, 1605, 1505, 1450, 1440, 1380, 1350, 1260, 1250, 1225, 1200, 1170, 1150, 1130, 1110, 1080, 1070, 965.

$^1$H NMR δCDCl$_3$/TMS (ppm) 3.80(2H, q, J=9Hz), 4.31 (2H, d, J=8Hz), 4.80(2H, s), 5.27(2H, s), 6.88(2H, d, J=9Hz), 7.20–7.60(7H, m).

As an isomer, 0.51 g of 2-4-(2,2,2-trifluoroethoxy)benzylimino)-3-(2,2,2-trifluoroethyl)-5-phenyltetrahydro-1,3,5-thiadiazin-4-one was obtained.

Melting point: 103.0–104.5° C.

IR $\nu^{KBr}_{max}$(cm$^{-1}$) 1675, 1605, 1500, 1430, 1375, 1350, 1285, 1260, 1230, 1190, 1160, 1150, 1135, 1100, 1060, 1035, 965.

$^1$H NMR δCDCl$_3$/TMS (ppm): 4.32(2H, q, J=8Hz), 4.47 (2H, s), 4.87(2H, s), 5.13(2H, d, J=10Hz), 6.94(2H, d, J=8Hz), 7.20–7.60(7H, m).

EXAMPLE 15

Synthesis of 2-(2,2,2-trifluoroethylimino)-3-[4-(1,1,2,2-tetrafluoroethoxy)benzyl]-5-(4-methylphenyl)-tetrahydro-1,3,5-thiadiazin-4-one (compound No. 171)

A solution of 0.65 g of trichloromethyl chloroformate in 20 ml of benzene was added dropwise to a solution of 0.76 9 of 1,3,5-tris(p-tolyl)hexahydro-s-triazine in 1ml of tetrahydrofuran at room temperature with stirring under a nitro9en current. rThe reaction solution was stirred at room temperature for 1 hour and then 2.20 9 of 1-4-(1,1,2,2-tetrafluoroethoxy)benzy]-3-(2,2,2-trifluoroethyl)thiourea was added at room temperature with stirring, and then 4 ml of triethylamine was added. The mixture was stirred at room temperature for 6 hours. Water (50 ml) was added to the reaction mixture, and the mixture was extracted with 200 ml of ethyl acetate. The ethyl acetate solution was washed with water and dried, and ethyl acetate was evaporated under reduced pressure. The resulting oily product was purified by column chromatography silica gel; developing solvent hexane/ethyl acetate (10:1)) to give 0.23 g of the captioned compound.

Refractive index $n^{20}_D$: 1.5242.

IR $\nu^{neat}_{max}$(cm$^{-1}$) 1680, 1615, 1510, 1450, 1390, 1360, 1285, 1270, 1265, 1210, 1190, 1145, 1130.

$^1$H NMR δCDCl$_3$/TMS (ppm): 2.37(3H, s), 3.80(2H, q, J=9Hz), 4.80(2H, s), 5.28(2H, s), 5.89(1H, tm, J=52Hz), 7.0–7.4(6H, m), 7.30(2H, d, J=8Hz).

As an isomer, 0.32 g of 2-4-(1,1,2,2-tetrafluoroethoxy)benzylimino]-3-(2,2,2-trifluoroethyl)-5-(4-methylphenyl)tetrahydro-1,3,5-thiadiazin-4-one was obtained.

Melting point: 89.0–90.5° C.

IR $\nu^{KBr}_{max}$(cm$^{-1}$) 1690, 1620, 1515, 1505, 1440, 1425, 1410, 1395, 1300, 1265, 1260, 1205, 1180, 1160, 1110.

$^1$H NMR δCDCl$_3$/TMS (ppm): 2.40(3H, s), 4.52(2H, s), 4.86(2H, s), 5.15(2H, q, J=10Hz), 5.93(1H, tm, J=52Hz), 7.10–7.50(8H, m).

EXAMPLE 16

Synthesis of 2-(2,2,2-trifluoroethylimino)-3-(4-pentafluoroethylbenzyl)-5-(4-methylphenyl)-tetrahydro-1,3,5-thiadiazin-4-one (compound No. 193)

0.71 g of N-chloromethyl-N-(4-methylphenyl)carbamoyl chloride and 1.20 g of 1-(4-pentafluoroethylbenzyl)-3-(2,2,2-trifluoroethyl)thiourea were dissolved in 30 ml of toluene, and the solution was heated under reflux for 4 hours. After the reaction, toluene was evaporated under reduced pressure. The resulting oily product was purified by column chromatography silica gel; developing solvent hexane/ethyl acetate (10:1)]to give 0.72 g of the captioned compound.

Refractive index $n^{20}_D$: 1.505

IR $\nu^{neat}_{max\,(cm^{-1})}$ 3030, 2930, 1680, 1610, 1515, 1450, 1390, 1290, 1260, 1200, 1140, 1105, 1095, 1045, 975, 940, 890, 845, 815, 750, 720.

$^1$H NMR δCDCl$_3$/TMS (ppm): 2.32(3H, s), 3.74(2H, q, J=8Hz), 4.74(2H, s), 5.24(2H, s), 7.17(4H, s), 7.28(2H, d, $J_{AB}$=2Hz), 7.38(2H, d, $J_{AB}$=2Hz).

As an isomer, 0.16 g of 2-(4-pentafluoroethylbenzylimino)-3-(2,2,2-trifluoroethyl)-5-(4-methylphenyl)-tetrahydro-1,3,5-thiadiazin-4-one was obtained. Melting point: 102.9–103.6° C.

IR $\nu^{KBr}_{max}$(cm$^{-1}$) 3030, 2980, 2800, 1700, 1625, 1510, 1450, 1395, 1335, 1290, 1260, 1210, 1170, 1120, 1050, 970, 950, 815, 750, 730.

$^1$H NMR δCDCl$_3$/TMS (ppm): 2.36(3H, s), 4.54(2H, s) 4.82(2H, s), 5.06(2H, q, J=8Hz), 7.18(4H, s), 7.44(2H, d, $J_{AB}$=8Hz).

EXAMPLE 17

Synthesis of 2-(2,2,2-trifluoroethylimino)-2-[4-(2-chloro-2-propeneoxy)benzyl-5-(4-methylphenyl)-tetrahydro-1,3,5-thiadiazin-4-one (compound No. 180)

0.65 g of N-chloromethyl-N-(4-methylphenyl)carbamoyl chloride and 1.0 g of 1-4-(2-chloro-2-propeneoxy)benzyl-3-(2,2,2-trifluoroethyl)thiourea were dissolved in 30 ml of toluene, and the solution was heated under reflux for 3 hours. After the reaction, toluene was evaporated under reduced pressure. The resulting oily product was purified by column chromatography [silica gel; developing solvent hexane/ethyl acetate (10:1)) to give 0.82 g of the captioned compound.

Refractive index $n^{20}_D$1.5641.

IR $\nu^{neat}_{max\,(cm^{-1})}$ 1680, 1610, 1510, 1450, 1390, 1360, 1290, 1265, 1240, 1210, 1170, 1140, 1090, 1045, 940, 890, 845, 820, 760, 745, 720.

$^1$H NMR δCDCl$_3$/TMS (ppm) 2.32(3H, s), 3.77(2H, q, J=10Hz), 4.52(2H, s), 4.72(2H, s), 5.20(2H, s), 5.40(1H, s), 5.54(1H, s), 6.86(2H, d, $J_{AB}$=9Hz), 7.10(4H, s), 7.48(2H, d, $J_{AB}$=9Hz).

As an isomer, 0.14 g of 2-[4-(2-chloro-2-propeneoxy)benzylimino)-3-(2,2,2-trifluoroethyl)-5-(4-methylphenyl)-tetrahydro-1,3,5-thiadiazin-4-one was obtained as a semisolid.

IR$\nu^{neat}_{max}$(cm$^{-1}$): 1690, 1615, 1510, 1440, 1390, 1300, 1260, 1220, 1160, 1115, 1160, 1115, 1045, 890, 820, 765, 720.

$^1$H NMR δCDCl$_3$/TMS (ppm): 2.36(3H, s), 4.46(2H, s) 4.60(2H, s), 4.80(2H, s), 507(2H, q, J=10Hz), 5.42(1H, s), 5.57(1H, s), 6.94(2H, d, $J_{AB}$=10Hz), 7.22(4H, s), 7.26(2H, d,

EXAMPLE 18

Synthesis of 2-(2,2,2-trifluoroethylimino)-3-(4-t-butoxycarbonylbenzyl)-5-(4-methylphenyl)-tetrahydro-1,3,5-thiadiazin-4-one (compound No. 215)

0.31 g of N-chloromethyl-N-(4-methylphenyl)carbamoyl chloride and 0.49 g of 1-(4-t-butoxycarbonylbenzyl)-3-(2,2,2-trifluoroethyl)thiourea were dissolved in 30 ml of benzene, and the solution was heated under reflux for 5 hours. After the reaction, benzene was evaporated under reduced pressure. The resulting oily product was purified by column chromatography [silica gel; developing solvent hexane/ethyl acetate (9:1)) to obtain 0.34 g of the captioned compound.

Refractive index $n^{20}{}_D$ 1.5329.

IR $\nu^{neat}{}_{max}$(cm$^{-1}$) 1700, 1670, 1605, 1505, 1440, 1380, 1360, 1305, 1290, 1260, 1200, 1160, 1140, 1110, 1085, 1040, 1010, 990, 930, 840, 810.

$^1$H NMR $\delta$CDCl$_3$/TMS (ppm): 1.57(9H, s), 2.35(3H, s), 3.77(2H, q, J=10Hz), 4.80(2H, s), 5.27(2H, s), 7.21(4H, s), 7.48(2H, d, J$_{AB}$=8Hz), 7.94(2H, As an isomer, 0.10 g of 2-(4-t-butoxycarbonylbenzylimino)-3-(2,2,2-trifluoroethyl)-5-(4-methylphenyl)-tetrahydro-1,3,5-thiadiazin-4-one was obtained.

Melting point: 105.0–108.0° C.

IR $\nu^{KBr}{}_{max}$(cm$^{-1}$) 1690, 1610, 1505, 1440, 1390, 1360, 1290, 1265, 1200, 1155, 1110, 1070, 1040, 1010, 980, 965, 840, 830, 810, 745.

$^1$H NMR $\delta$CDCl$_3$/TMS (ppm): 1.60(9H, s), 2.37(3H, s), 4.56(2H, s), 4.84(2H, s), 5.09(2H, q, J=10Hz), 7.24(4H, s), 7.43(2H, d, J$_{AB}$=9Hz), 8.04(2H, d, J$_{AB}$=9Hz).

EXAMPLE 19

Synthesis of 2-(2,2,2-trifluoroethylimino)-3-(4-trifluoromethoxybenzyl)-5-(2-fluoro-4-methylphenyl)-tetrahydro-1,3,5-thiadiazin-4-one (compound No. 237)

0.60 g of N-chloromethyl-N-(2-fluoro-4-methylphenyl)carbamoyl chloride and 0.84 g of 1-(4-trifluoromethoxybenzyl)-3-(2,2,2-trifluoroethyl)thiourea were dissolved in 50 ml of toluene, and the solution was heated under reflux for 5 hours. After the reaction, toluene was evaporated under reduced pressure. The resulting oily product was purified by column chromatography silica gel; developing solvent hexane/ethyl acetate (9:1)) to give 0.68 g of the captioned compound.

Refractive index $n^{20}{}_D$: 1.5180.

IR $\nu^{neat}{}_{max}$(cm$^{-1}$) 1685, 1615, 1510, 1450, 1390, 1360, 1260, 1220, 1140, 1100, 1080, 1040, 1015, 935, 840, 810, 745.

$^1$H NMR $\delta$CDCl$_3$/TMS (ppm): 2.36(3H, s), 3.76(2H, q, J=9.6Hz), 4.70(2H, s), 5.20(2H, s), 6.92–7.24 (5H, m), 7.43(2H, d, J=9Hz).

As an isomer, 0.17 g of 2-(4-trifluoromethoxybenzylimino)-3-(2,2,2-trifluoroethyl)-5-(2-fluoro-4-methylphenyl)-tetrahydro-1,3,5-thiadiazin-4-one was obtained as a semisolid.

IR $\nu^{neat}{}_{max}$(cm$^{-1}$) 1710, 1615, 1590, 1510, 1445, 1390, 1360, 1330, 1270, 1250, 1220, 1150, 1105, 1035, 830, 815, 755.

$^1$H NMR $\delta$CDCl$_3$/TMS (ppm): 2.38(3H, s), 4.52(2H, s), 4.76(2H, s), 5.08(2H, d, J=9Hz), 6.91–7.37 (7H, m).

EXAMPLE 20

Synthesis of 2-(2,2,2-trifluoroethylimino)-3-fluoro-4-(2,2,2-trifluoroethoxy)benzyl]-5-(4-methylphenyl)-tetrahydro-1,3,5-thiadiazin-4-one (compound No. 281)

0.6 g of N-chloromethyl-N-(4-methylphenyl)carbamoyl chloride and 1.00 g of 1-[3-fluoro-4-(trifluoroethoxy)benzyl-3-(2,2,2-trifluoro-ethyl)thiourea were dissolved in 50 ml of toluene, and the solution was heated under reflux for 3 hours. After the reaction, toluene was evaporated under reduced pressure. The resulting oily product was purified by column chromatography silica gel; developing solvent hexane/ethyl acetate (4:1)] to give 0.63 g of the captioned compound.

Melting point: 94.1–95.6° C.

IR $\nu^{KBr}{}_{max}$(cm$^{-1}$) 1665, 1605, 1515, 1465, 1440, 1425, 1410, 1315, 1290, 1265, 1170, 1145, 1125, 965, 935, 830, 765, 755.

$^1$H NMR $\delta$CDCl$_3$/TMS (ppm): 2.36(3H, s), 3.81(2H, q, J=9Hz), 4.37(2H, q, J=8Hz), 4.80(2H, s), 5.16(2H, s), 6.90–7.40(7H, m).

As an isomer, 0.04 g of 2-3-fluoro-4-(2,2,2-trifluoroethoxy)benzylimino-3-(2,2,2-trifluoroethyl)-(4-methylphenyl)-tetrahydro-1,3,5-thiadiazin-4-one was obtained.

Refractive index $n^{20}{}_D$: 1.5196.

IR $\nu^{KBr}{}_{max}$ (cm$^{-1}$): 1690, 1620, 1515, 1445, 1395, 1290, 1265, 1215, 1165, 1115, 1055, 975, 865, 820, 775.

$^1$H NMR$\delta$CDCl$_3$/TMS (ppm): 2.35(3H, s), 4.39(2H, q, J=8Hz), 4.44(2H, s), 4.82(2H, s), 5.06 (2H, q, J=9Hz), 7.00–7.30(7H, m).

Table 2 below shows the $^1$H NMR data, IR data and properties of compounds produced by methods substantially in accordance with the methods described in Examples 1 to 20.

TABLE 2

| Compound No. | $^1$H NMR$\delta_{TMS}{}^{CDCl_3}$ (ppm) | IR$\nu_{max}$ (cm$^{-1}$) | Melting point or refractive index |
|---|---|---|---|
| 1 | 2.28 (3H, s), 3.67 (2H, q, J=9Hz), 4.65 (2H, s), 5.18 (2H, s), 6.90–7.26 (9H, m) <CDCl$_3$> | 1680, 1610, 1500, 1450, 1390, 1360, 1270, 1205, 1140, 1090, 1040, 935, 845, 755, 715, 690 <neat> | Semisolid |
| 2 | 1.23 (3H, t, J=7Hz), 2.65 (2H, q, J=7Hz), 3.83 (2H, q, J=8Hz), 4.80 (2H, s), 5.30 (2H, s), 6.70–7.50 (9H, m) <CDCl$_3$> | 1685, 1610, 1500, 1445, 1390, 1345, 1265, 1150, 1090, 1035, 970, 940, 845, 825, 775, 755 <neat> | Refractive index $n_D{}^{20}$ 1.5726 |
| 3 | 1.24 (6H, d, J=8Hz), 2.68–3.07 (1H, m), 3.76 (2H, q, J=9Hz), 4.80 (2H, s), 5.32 (2H, s), 7.12–7.44 (9H, m) <CDCl$_3$> | 1680, 1610, 1490, 1440, 1390, 1270, 1260, 1200, 1140, 1090, 1055, 1040, 940, 890, 845, 760 <neat> | Semisolid |
| 4 | 0.80–1.00 (3H, m), 1.10–1.70 | 1680, 1610, 1495, 1440, 1380, | Refractive |

TABLE 2-continued

| Compound No. | $^1\text{H NMR}\delta_{TMS}^{CDCl_3}$ (ppm) | $\text{IR}\nu_{max}$ (cm$^{-1}$) | Melting point or refractive index |
|---|---|---|---|
|  | (4H, m), 2.58 (2H, t, J=7Hz), 3.76 (2H, q, J=8Hz), 4.80 (2H, s), 5.30 (2H, s), 6.60–7.40 (9H, m)<br><CDCl$_3$> | 1340, 1260, 1200, 1140, 1090, 1035, 935, 840, 750<br><neat> | index $n_D^{20}$ 1.5501 |
| 5 | 0.80 (3H, t, J=6Hz), 1.12–1.24 (3H, m), 1.42–1.68 (2H, m), 2.34–2.62 (1H, m), 3.75 (2H, q, J=9Hz), 4.75 (2H, s), 5.16 (2H, s), 6.94–7.25 (9H, m)<br><CDCl$_3$> | 1680, 1625, 1550, 1500, 1450, 1390, 1280, 1265, 1200, 1140, 1090, 1040, 935, 845, 755<br><neat> | Semisolid |
| 7 | 2.30 (3H, s), 2.37 (3H, s), 3.80 (2H, q, J=8Hz), 4.77 (2H, s), 5.32 (2H, s), 7.00–7.50 (8H, m)<br><CDCl$_3$> | 1690, 1610, 1510, 1445, 1390, 1290, 1265, 1205, 1140, 1090, 1040, 1020, 940, 740, 705<br><neat> | Semisolid |
| 9 | 1.20 (3H, s), 1.33 (3H, s), 2.40 (3H, s), 2.87 (1H, d, q, J=7Hz, J=5Hz), 3.87 (2H, q, J=8Hz), 4.86 (2H, s), 5.33 (2H, s), 7.20 (2H, d, J=6Hz), 7.23 (4H, s), 7.50 (2H, d, J=6Hz)<br><CDCl$_3$> | 1670, 1610, 1510, 1455, 1395, 1365, 1280, 1265, 1210, 1145, 1125, 1085, 1040, 940, 880, 845, 820, 755, 720<br><KBr> | Melting point 84.5–86.0° C. |
| 18 | 1.32 (9H, s), 3.80 (2H, q, J=9Hz), 4.73 (2H, s), 5.27 (2H, s), 7.00–7.50 (8H, m)<br><CDCl$_3$> | 1680, 1610, 1515, 1500, 1460, 1440, 1400, 1385, 1360, 1270, 1260, 1255, 1235, 1130, 1090, 1040, 1020, 940<br><neat> | Refractive index $n_D^{20}$ 1.5455 |
| 21 | 1.26 (9H, s), 2.33 (3H, s), 3.76 (2H, q, J=9Hz), 4.64 (2H, s), 5.22 (2H, s), 6.88–7.43 (7H, m)<br><CDCl$_3$> | 1890, 1620, 1520, 1450, 1400, 1370, 1290, 1275, 1210, 1150, 1090, 940, 850, 820, 760, 730 710<br><KBr> | Melting point 114–116° C. |
| 26 | 1.35 (3H, t, J=8Hz), 2.30 (3H, s), 3.74 (2H, q, J=8Hz), 3.93 (2H, q, J=8Hz), 4.62 (2H, s), 4.14 (2H, s), 6.72 (2H, d, J=8Hz), 7.10 (4H, s), 7.29 (2H, d, J=8Hz)<br><CDCl$_3$> | 1680, 1610, 1515, 1445, 1390, 1290, 1270, 1245, 1205, 1175, 1140, 1085, 1045, 935, 845, 815, 740<br><neat> | Refractive index $n_D^{20}$ 1.5535 |
| 28 | 0.84–0.99 (3H, m), 1.25–1.50 (4H, m), 1.60–1.88 (2H, m), 2.36 (3H, s), 3.74 (2H, t, J=9Hz), 3.87 (2H, q, 7=9Hz), 4.72 (2H, s), 5.24 (2H, s), 6.80 (2H, d, J=8Hz), 7.18 (4H, s), 7.43 (2H, d, J=8Hz)<br><CDCl$_3$> | 1670, 1610, 1460, 1440, 1400, 1320, 1270, 1150, 1100, 1060, 1010, 970, 885, 825, 810, 760<br><neat> | Refractive index $n_D^{20}$ 1.5397 |
| 29 | 3.41 (2H, q, J=9Hz), 4.74 (2H, s), 5.20 (2H, s), 7.00–7.50 (9H, m)<br><CDCl$_3$> | 1685, 1620, 1505, 1495, 1450, 1390, 1365, 1290, 1280, 1270, 1210, 1150, 1095<br><neat> | Refractive index $N_D^{20}$ 1.5737 |
| 30 | 3.73 (2H, q, J=9Hz), 4.77 (2H, s), 5.14 (2H, s), 7.00–7.50 (9H, m)<br><CDCl$_3$> | 1680, 1615, 1500, 1490, 1450, 1390, 1275, 1210, 1150, 1130, 1110, 1090, 1070, 1045, 1015, 940<br><neat> | Refractive index $N_D^{20}$ 1.5732 |
| 31 | 2.38 (3H, s), 3.77 (2H, q, J=9Hz), 4.75 (2H, s), 5.24 (2H, s), 7.14–7.46 (8H, m)<br><CDCl$_3$> | 1680, 1610, 1510, 1490, 1450, 1380, 1350, 1270, 1260, 1210, 1160, 1090, 1040, 1015, 935, 890, 850, 820, 800<br><neat> | Semisolid |
| 36 | 2.34 (3H, s), 3.74 (2H, q, J=10Hz), 4.76 (2H, s), 5.11 (2H, s), 7.12–7.50 (7H, m)<br><CDCl$_3$> | 1690, 1675, 1650, 1615, 1520, 1475, 1400, 1270, 1150, 1125, 1095, 1035, 935, 825, 760, 740, 690, 670<br><KBr> | Melting point 108.6–110.1° C. |
| 44 | 3.78 (2H, q, J=9Hz), 4.80 (2H, s), 5.23 (2H, s), 6.79–7.56 (12H, m)<br><CDCl$_3$> | 1680, 1610, 1505, 1445, 1390, 1260, 1140, 1095, 1040, 935, 840, 690<br><neat> | Semisolid |
| 47 | 3.88 (2H, q, J=9Hz), 4.89 (2H, s), 5.11 (2H, s), 5.31 (2H, s), 6.98 (2H, d, J=9Hz), 7.10–7.60 (12H, m)<br><CDCl$_3$> | 1675, 1610, 1505, 1450, 1385, 1270, 1260, 1140, 1090, 1040, 1025<br><neat> | Refractive index $n_D^{20}$ 1.5892 |
| 48 | 2.36 (3H, s), 3.89 (2H, q, J=9Hz), 4.72 (2H, s), 5.04 (2H, s), 5.27 (2H, s), 6.80–7.56 (13H, m)<br><CDCl$_3$> | 1680, 1610, 1515, 1455, 1390, 1270, 1145, 1090, 940, 820, 750, 695<br><neat> | Refractive index $n_D^{20}$ 1.5720 |
| 70 | 3.85 (2H, q, J=9Hz), 4.84 (2H, s), 5.31 (2H, s), 6.54 (1H, t, J=74Hz), 7.05–7.61 (9H, m)<br><CDCl$_3$> | 1680, 1615, 1510, 1450, 1390, 1260, 1130, 1090, 1040, 930, 840<br><neat> | Refractive index $n_D^{20}$ 1.5361 |

TABLE 2-continued

| Compound No. | $^1$H NMR$\delta_{TMS}^{CDCl_3}$ (ppm) | IR$\nu_{max}$ (cm$^{-1}$) | Melting point or refractive index |
|---|---|---|---|
| 73 | 3.81 (2H, q, J=9Hz), 4.85 (2H, s), 5.31 (2H, s), 7.03–7.65 (9H, m) | 1685, 1620, 1500, 1450, 1390, 1275, 1215, 1150, 1050, 870, 760, 695 <neat> | |
| 76 | 3.85 (2H, q, J=9Hz), 4.86 (2H, s), 5.35 (2H, s), 5.98 (1H, tm, J=52Hz), 7.10–7.80 (9H, m) | 1670, 1610, 1500, 1490, 1440, 1380, 1280, 1265, 1255, 1250, 1235, 1220, 1090, 1080 <neat> | Refractive index $n_D^{20}$ 1.5160 |
| 77 | 3.81 (2H, q, J=9.2Hz), 4.31 (2H, tm, 8.3Hz), 4.83 (2H, s), 5.23 (2H, s), 6.01 (2H, tt, J=53.1, 5.4Hz), 6.80–7.50 (9H, m) | 1680, 1610, 1510, 1490, 1450, 1425, 1390, 1360, 1290, 1255, 1205, 1175, 1090, 1070, 1040, 940, 845, 830 <neat> | Refractive index $n_D^{20}$ 1.5300 |
| 81 | 3.82 (2H, q, J=8Hz), 4.66 (2H, s), 4.83 (2H, s), 5.30 (2H, s), 7.10–7.60 (9H, m) | 1700, 1680, 1610, 1490, 1445, 1405, 1380, 1360, 1290, 1275, 1260, 1255, 1220, 1205, 1170, 1085, 1010, 995, 965, 935, 840, 825 <neat> | Refractive index $n_D^{20}$ 1.5296 |
| 82 | 3.80 (2H, q, J=9Hz), 4.85 (2H, s), 5.25 (2H, s), 6.80–7.60 (9H, m) | 1680, 1610, 1500, 1445, 1390, 1360, 1285, 1270, 1205, 1170, 1140, 1090, 970, 845 <neat> | Refractive index $n_D^{20}$ 1.5744 |
| 85 | 3.84 (2H, q, J=8Hz), 4.58 (2H, s), 4.78 (2H, s), 5.24 (2H, s), 5.43 (1H, s), 5.55 (1H, s), 6.84 (2H, d, $J_{AB}$=9Hz), 7.10–7.50 (7H, m) | 1670, 1605, 1505, 1485, 1440, 1385, 1350, 1280, 1260, 1215, 1140, 1080, 1040, 1010, 930, 885, 825, 755, 720 <neat> | Refractive index $n_D^{20}$ 1.5738 |
| 90 | 3.79 (2H, q, J=9Hz), 4.85 (2H, s), 5.26 (2H, s), 6.76 (1H, t, J=57Hz), 7.20–7.52 (9H, m) | 1680, 1615, 1500, 1425, 1390, 1260, 1205, 1125, 1065, 940, 840, 750, 690 <neat> | Melting point 70–75° C. |
| 92 | 3.81 (2H, q, J=9Hz), 4.86 (2H, s), 5.32 (2H, s), 7.15–7.72 (9H, m) | 1680, 1615, 1500, 1385, 1260, 1140, 1060, 930, 835 <neat> | Refractive index $n_D^{20}$ 1.5774 |
| 93 | 3.78 (2H, q, J=9Hz), 4.83 (2H, s), 5.29 (2H, s), 7.16–7.69 (9H, m) | 1685, 1620, 1505, 1450, 1395, 1270, 1150, 1095, 890, 695 <neat> | Refractive index $n_D^{20}$ 1.5650 |
| 98 | 3.74 (2H, q, J=8Hz), 4.74 (2H, s), 5.22 (2H, s), 7.16 (2H, d, $J_{AB}$=8Hz), 7.32 (2H, d, $J_{AB}$=8Hz), 7.48 (5H, s) | 2940, 1690, 1620, 1495, 1450, 1390, 1290, 1260, 1210, 1145, 1095, 1020, 980, 940, 830, 750, 730 <neat> | Refractive index $n_D^{20}$ 1.5269 |
| 99 | 3.77 (2H, q, J=9Hz), 5.33 (2H, s), 4.90 (2H, s), 7.20–7.70 (9H, m) | 1500, 1450, 1405, 1390, 1350, 1270, 1260, 1230, 1210, 1180, 1145, 1115, 1095, 1065, 1040, 1020, 930, 900 <neat> | Refractive index $n_D^{20}$ 1.4962 |
| 101 | 3.80 (2H, q, J=9Hz), 4.87 (2H, s), 5.31 (2H, s), 7.30–7.80 (9H, m) | 1680, 1610, 1500, 1490, 1445, 1390, 1360, 1280, 1200, 1140, 1105, 1090 <neat> | Refractive index $n_D^{20}$ 1.4814 |
| 102 | 3.51 (2H, s), 3.78 (2H, q, J=9.2Hz), 4.78 (2H, s), 5.26 (2H, s), 7.10–7.60 (9H, m) | 1685, 1620, 1500, 1450, 1390, 1365, 1335, 1280, 1270, 1260, 1220, 1175, 1150, 1120, 1095, 1050, 980 <neat> | Refractive index $n_D^{20}$ 1.4857 |
| 104 | 3.79 (2H, q, J=9Hz), 4.82 (2H, s), 4.26 (2H, s), 6.79 (1H, s), 7.10–7.70 (9H, m) | 1680, 1620, 1495, 1440, 1390, 1290, 1265, 1210, 1160, 1140, 1080 <KBr> | Semisolid |
| 120 | 1.59 (9H, s), 3.77 (3H, q, J=9Hz), 4.84 (2H, s), 5.35 (2H, s), 7.10–7.60 (7H, m), 7.92 (2H, d, J=8Hz) | 1700, 1680, 1610, 1495, 1440, 1385, 1365, 1305, 1290, 1270, 1260, 1250, 1205, 1160, 1140, 1115, 1090 <neat> | Refractive index $n_D^{20}$ 1.5650 |
| 125 | 3.83 (2H, q, J=9Hz), 4.86 (2H, s), 5.37 (2H, s), 7.00–7.80 (9H, m), 8.01 (1H, m), 8.31 (1H, m) | 1700, 1620, 1510, 1465, 1300, 1330, 1310, 1265, 1195, 1165, 1120, 1095, 1070, 835 <neat> | Refractive index $n_D^{20}$ 1.5646 |
| 166 | 2.36 (3H, s), 3.76 (2H, q, J=9Hz), 4.78 (2H, s), 5.28 (2H, s), 7.08–7.56 (8H, m) | 1680, 1615, 1510, 1440, 1390, 1260, 1140, 1080, 1015, 935, 840, 815 <neat> | Refractive index $n_D^{20}$ 1.5227 |
| 170 | 2.39 (3H, s), 3.84 (2H, q, J=9Hz), 4.35 (2H, q, J=8Hz), 4.83 (2H, s), 5.31 (2H, s), 6.91 (2H, d, J=8Hz), 7.10–7.40 (4H, m), 7.54 (2H, d, J=8Hz) | 1670, 1600, 1510, 1400, 1380, 1280, 1260, 1230, 1200, 1170, 1140, 1120, 1105, 1070 <neat> | Melting point 130.0–131.0° C. |

TABLE 2-continued

| Compound No. | $^1$H NMR$\delta_{TMS}^{CDCl_3}$ (ppm) | IR$\nu_{max}$ (cm$^{-1}$) | Melting point or refractive index |
|---|---|---|---|
| 172 | 2.38 (3H, s), 3.83 (2H, q, J=9Hz), 4.33 (2H, tm, J=11Hz), 4.79 (2H, s), 5.23 (2H, s), 6.12 (2H, tt, J=54Hz, 8Hz), 6.80–7.70 (8H, m) | 1685, 1620, 1515, 1450, 1390, 1365, 1290, 1275, 1265, 1260, 1210, 1080, 1050, 1015, 1095, 940, 835 <neat> | Refractive index n$_D^{20}$ 1.5279 |
| 177 | 2.36 (3H, s), 3.81 (2H, q, J=9.1Hz), 4.81 (2H, s), 5.24 (2H, s), 6.94 (2H, d, J=8.9Hz), 7.17 (2H, d, J=8.6Hz), 7.21 (2H, d, J=8.6Hz), 7.50 (2H, d, J=8.9Hz) | 1680, 1610, 1585, 1515, 1495, 1450, 1390, 1360, 1290, 1275, 1260, 1240, 1220, 1205, 1170, 1150, 1110, 1090, 1045, 1020, 940, 845, 820 <neat> | Refractive index n$_D^{20}$ 1.5627 |
| 181 | 2.36 (1H, s), 3.83 (2H, q, J=10Hz), 4.65 (2H, d, J=1Hz), 4.81 (2H, s), 5.25 (2H, s), 5.65–5.70 (1H, m), 6.00–6.03 (1H, m), 6.85 (2H, d, J$_{AB}$=9Hz), 7.22 (4H, s), 7.45 (2H, d, J$_{AB}$=9Hz) | 1690, 1615, 1520, 1450, 1395, 1365, 1290, 1220, 1140, 1090, 1045, 940, 900, 850, 825, 750, 670 <neat> | Refractive index n$_D^{20}$ 1.5650 |
| 182 | 2.35 (3H, s), 3.80 (2H, q, J=8.9Hz), 4.62 (2H, d, J=1.5Hz), 4.78 (2H, s), 5.21 (2H, s), 6.56 (1H, t, J=1.5Hz), 6.82 (2H, d, J$_{AB}$=8.4Hz), 7.15–7.22 (4H, m), 7.42 (2H, d, J$_{AB}$=8.4Hz) | 1680, 1610, 1510, 1450, 1390, 1360, 1290, 1270, 1240, 1210, 1175, 1145, 1090, 1030, 930, 820 <neat> | Refractive index n$_D^{20}$ 1.5644 |
| 183 | 2.35 (3H, s), 3.80 (2H, q, J=8.9Hz), 4.77 (2H, s), 4.81 (2H, s), 5.22 (2H, s), 6.39 (1H, s), 6.86 (2H, d, J$_{AB}$=8.9Hz), 7.15–7.21 (4H, m), 7.42 (2H, d, J$_{AB}$=8.9Hz) | 1670, 1600, 1495, 1430, 1375, 1275, 1250, 1195, 1160, 1130, 1070, 1020, 920, 800 <neat> | Melting point 86.7–87.7° C. |
| 185 | 2.44 (3H, s), 3.91 (3H, q, J=9Hz), 4.98 (2H, s), 5.43 (2H, s), 7.01 (1H, t, J=59Hz), 7.43 (4H, s), 7.74 (4H, s) | 1680, 1610, 1510, 1490, 1445, 1385, 1260, 1205, 1140, 1060, 935, 890, 840, 815, 750 <neat> | Melting point 85.0–88.0° C. |
| 186 | 2.38 (3H, s), 3.81 (2H, q, J=9Hz), 4.83 (2H, s), 5.33 (2H, s), 7.24 (4H, s), 7.50–7.70 (4H, m) | 1680, 1620, 1510, 1490, 1445, 1390, 1260, 1210, 1085, 1045, 1015, 935, 845, 815, 750 <neat> | Refractive index n$_D^{20}$ 1.5406 |
| 187 | 2.35 (3H, s), 3.76 (2H, q, J=9Hz), 4.81 (2H, s), 5.24 (2H, s), 7.18 (4H, s), 7.40–7.63 (4H, m) | 1695, 1620, 1515, 1450, 1390, 1275, 1260, 1155, 1040, 935, 840, 740 <KBr> | Melting point 74.0–76.0° C. |
| 194 | 2.36 (3H, s), 3.79 (2H, q, J=9.2Hz), 4.85 (2H, s), 5.30 (2H, s), 7.18 (2H, d, J=8.4Hz), 7.22 (2H, d, J=8.4Hz), 7.50 (2H, d, J=8.4Hz), 7.57 (2H, d, J=8.4Hz) | 1685, 1620, 1515, 1450, 1395, 1350, 1290, 1275, 1230, 1210, 1180, 1150, 1120 <neat> | Refractive index n$_D^{20}$ 1.4992 |
| 196 | 2.37 (3H, s), 3.83 (2H, q, J=9Hz), 4.86 (2H, s), 5.31 (2H, s), 7.10–7.70 (8H, m) | 1685, 1620, 1515, 1450, 1395, 1365, 1290, 1275, 1270, 1260, 1240, 1205, 1175, 1150, 1115, 1095 <neat> | Refractive index n$_D^{20}$ 1.4757 |
| 220 | 2.36 (3H, s), 3.83 (2H, q, J=9Hz), 4.80 (2H, s), 5.29 (2H, s), 7.12 (2H, d, J$_{AB}$=8Hz), 7.10–7.30 (4H, m), 7.63 (2H, d, J$_{AB}$=8Hz), 8.00 (1H, m), 8.32 (1H, m) | 1680, 1615, 1510, 1460, 1390, 1325, 1285, 1260, 1195, 1165, 1130, 1090, 1070, 1020, 940, 915, 845, 820, 750, 730 <neat> | Refractive index n$_D^{20}$ 1.5449 |
| 221 | 3.85 (2H, q, J=9Hz), 4.79 (2H, s), 5.33 (2H, s), 6.58 (1H, t, J=75Hz), 7.05–7.59 (8H, m) | 1680, 1610, 1505, 1495, 1440, 1385, 1280, 1255, 1210, 1120, 1075, 1035, 930, 835, 820, 745 <neat> | Refractive index n$_D^{20}$ 1.5209 |
| 245 | 3.84 (2H, q, J=8Hz), 4.77 (2H, s), 5.32 (2H, s), 7.00–7.60 (7H, m) | 1690, 1620, 1510, 1480, 1455, 1395, 1275, 1220, 1150, 1015, 940, 845, 790, 710 <neat> | Refractive index n$_D^{20}$ 1.5107 |
| 258 | 3.78 (2H, q, J=10Hz), 4.36 (2H, q, J=8Hz), 4.85 (2H, s), 5.17 (2H, s), 6.30–7.50 (8H, m) | 1680, 1620, 1595, 1515, 1390, 1290, 1265, 1210, 1160, 1150, 1130 <neat> | Refractive index n$_D^{20}$ 1.5335 |

The following Referential Examples illustrate the production of the starting materials for the compounds provided by this invention.

REFERENTIAL EXAMPLE 1

Synthesis of 1-(4-t-butylbenzyl)-3-(2,2,2-trifluoroethyl)thiourea (1) 8.16 g of 4-t-butylbenzylamine was added dropwise at −10° C. with stirring to a mixture of 10.32 g of dicyclohexylcarbodiimide (DCC), 20 ml of carbon disulfide and 100 ml of diethyl ether. The temperature of the mixture was returned to room temperature, and it was left to stand for 12 hours. The reaction solution was filtered, and the residue was washed with diethyl ether. The filtrate was combined with the washing, and the solvent was evaporated under reduced pressure. The resulting oily product was purified by column chromatography silica gel; developing solvent hexane/ethyl acetate (19:1) to give 8.41 g of the desired 4-t-butylbenzyl isothiocyanate.

Melting point: 44.0–47.0° C.

IR $\nu^{KBr}_{max}$(cm$^{-1}$) 2940, 2850, 2170, 2100, 1510, 1460, 1410, 1340, 1305, 1280, 1270, 1210, 1200, 1110, 1085, 1020, 805, 710, 540.

$^1$H NMR $\delta$CDCl$_3$/TMS (ppm): 1.34(9H, s), 4.64(2H, s), 7.22(2H, d, J=8Hz), 7.37(2H, d, J=8Hz).

Reference: Angewandte Chemie International Edition, Vol. 6, page 174 (1967).

(2) 10.82 g of 4-t-butylbenzoyl isothiocyanate obtawined in (1) and 7.54 g of 2,2,2-trifluoroethylamine were dissolved in 20 ml of ethyl acetawte. The solution was left to stand at room temperature for 24 houirs. Ethyl acetate was evaporated under reduced prerssure. The resultilng oily product was purified by column chromatography silica gel; developing solvent hexane/ethyl acetate (4:1)) to give 15.80 g of the desired 1-(4-t-butylbenzyl)-3-(2,2,2-trifluoroethyl)thiourea.

Melting point: 101.0–103.0° C.

IR$\nu^{neat}_{max}$(cm$^{-1}$) 3260, 3085, 2950, 1570, 1380, 1350, 1320, 1300, 1290, 1255, 1155, 1125, 1050, 970, 935, 830.

$^1$H NMR $\delta$CDCl$_3$/TMS (ppm): 1.34(9H, s), 4.30(2 4.5–4.7(2H, m), 5.8–6.2(1H, br), 6.4–6.8(1H, br), 7.23(2H, d, J=9Hz), 7.37(2H, d, J=9Hz).

REFERENTIAL EXAMPLE 2

Synthesis of 1-(4-trifluoromethylbenzyl)-3-(2,2,2-trifluoroethyl)thiourea (1) 4-Trifluoromethylbenzyl isothiocyanate 10 g of 4-trifluoromethylbenzylamine was added dropwise at −10° C. with stirring to a mixture of 11.78 g of DCC, 25 ml of carbon disulfide and 50 ml of diethyl ether. The temperature of the mixture was returned to room temperature, and it was left to stand for 12 hours. The reaction solution was filtered, and the residue was washed with diethyl ether. The filtrate and the washing were combined, and the solvent was evaporated under reduced pressure. The resulting oily product was purified by column chromatography silica gel; developing solvent hexane/ethyl acetate (10:1)]to give 11.15 g of the desired 4-trifluoromethylbenzyl isothiocyanate.

Refractive index n$^{20}_D$: 1.5270.

IR $\nu^{neat}_{max}$(cm$^{-1}$) 2930, 2180, 2090, 1690, 1620, 1420, 1325, 1165, 1125, 1065, 1020, 815.

$^1$H NMR $\delta$CDCl$_3$/TMS (ppm): 4.74(2H, s), 7.47(2H, d, J=8Hz), 7.66(2H, d, J=8Hz).

(2) 1-(4-Trifluoromethylbenzyl)-3-(2,2,2-trifluoroethyl)thiourea 7.0 g of the 4-trifluoromethylbenzyl)3-(2,2,2-trifluoroethyl)thiourea obtained in (1) and 3.83 g of 2,2,2-trifluoroethylamine were dissolved in 50 ml of ethyl acetate, and the solution was left to stand at room temperature for 24 hours. Ethyl acetate was evaporated under reduced pressure. The resulting white crystals were recrystallized form hexane to give 8.79 g of the desired 1-(4-trifluoromethylbenzyl)-3-(2,2,2-trifluoroethyl)thiourea.

Melting point: 80.0–82.0° C.

IR $\nu^{KBr}_{max}$(cm$^{-1}$) 3230, 3070, 1615, 1570, 1550, 1390, 1380, 1345, 1320, 1305, 1280, 1245, 1160, 1115, 1105, 1060.

$^1$H NMR $\delta$CDCl$_3$/TMS (ppm): 4.08–4,40(2H, m), 4.76 (2H, d, J=6Hz), 6.02(1H, m), 6.56(1H, m), 7.38(2H, d, J=8Hz). 7.57(2H, d, J=8Hz).

REFERENTIAL EXAMPLE 3

Synthesis of 1-(4-trifluoromethoxybenzyl)-3-(2,2,2-trifluoroethyl)-thiourea (1) N-(4-trifluoromethoxybenzyl)phthalimide Phosphorus tribromide (5.17 g) was added dropwise to 10.0 g of 4-trifluoromethoxybenzyl alcohol at oC over 10 minutes, and the mixture was stirred at room temperature for 2 hours. The reaction solution was poured into ice water, and extracted with 100 ml of hexane. The hexane solution was washed with water and dried, and hexane was evaporated under reduced pressure to give 13.13 g of white crystals. The crystals were dissolved in 60 ml of dimethylformamide, and 19.26 g of potassium phthalimide and 1 g of potassium iodide were added, and the mixture was heated at 100 oC for 3 hours with stirring. Water (50 ml) was added to the reaction solution, and the mixture was extracted with 200 ml of ethyl acetate. The ethyl acetate solution was washed with water and dried. Ethyl acetate was evaporated under reduced pressure. The resulting oily product was purified by column chromatography silica gel; developing solvent hexane/ethyl acetate (5:1)) to give 14.17 g of the captioned compound.

Melting point: 82.1–83.6° C.

IR $\nu^{KBr}_{max}$(cm$^{-1}$) 1690, 1620, 1515, 1505, 1440, 1425, 1410, 1395, 1300, 1265, 1260, 1205, 1180, 1160, 1110.

$^1$H NMR $\delta$CDCl$_3$/TMS (ppm): 4.83(2H, s), 7.04-7.85(8H, m).

(2) 4-Trifluoromethoxybenzyl isothiocyanate 12 g of N-(4-trifluoromethoxybenyl)phthalimide was dissolved in 50 ml of ethanol, and 2.34 g of hydrazine hydrate was added dropwise. Then, the mixture was heated under reflux for 4 hours and then allowed to cool. Concentric hydrochloric acid (10 ml) was added, and the mixture was filtered. The ethanol solution as the filtrate was evaporated under reduced pressure, and the residue was adjusted to pH 11 by adding an aqueous solution of sodium hydroxide. Ethyl acetate (100 ml) was added, and the solution was washed with water and dried. Ethyl acetate was evaporated under reduced pressure to give 6.55 g of an oily product. The resulting oily product (6.55 g) was added dropwise to a mixture of 10.32 g of dicyclohexylcarbodiimide (DCC), 20 ml of carbon disulfide and 100 ml of ethyl ether with stirring at −10° C. The temperature was returned to room temperature, and the mixture was left to stand for 12 hours.

The reaction mixture was filtered, and the residue was washed with ethyl ether, and combined with the filtrate. The solvent was evaporated under reduced pressure. The resulting oily product was purified by column chromatography silica gel; developing solvent hexane/ethyl acetate (19:1)) to give 7.53 g of the captioned compound.

IR $\nu^{neat}_{max}$(cm$^{-1}$) 2080, 1510, 1440, 1340, 1260, 1215, 1160, 1015, 920.

$^1$H NMR $\delta$CDCl$_3$/TMS (ppm): 4.69(2H, s), 7.28(2H, d, J$_{AB}$=9Hz), 7.40(2H, d, J$_{AB}$=9Hz).

(3) 1-(4-trifluoromethoxybenzyl)-3-(2,2,2-trifluoroethyl)thiourea.

6.0 g 4-trifluoromethoxybenzyl isothiocyanate obtained in (2) above and 3.06 g of 2,2,2-trifluoroethylamine were dissolved in 50 ml of ethyl acetate, and the solution was left to stand at room temperature for 24 hours. Ethyl acetate was evaporated under reduced pressure, and the resulting white crystals were recrystallized from hexane to give 6.05 g of the captioned compound.

Melting point: 94.7–96.4° C.

IR $\nu^{neat}_{max}$(cm$^{-1}$) 3240, 3060, 1570, 1510, 1300, 1250, 1180, 1170, 1150, 1110, 975, 920, 825, $^{d1}$H NMR $\delta$CDCl$_3$/TMS (ppm): 4.31(2H, d, J=9Hz), 4.66 (2H, s), 6.30(1H, m), 6.74(1H, m), 7.12-7.55 (9H, m).

REFERENTIAL EXAMPLE 4

Synthesis of 1-(4-trifluoromethylthiobenzyl)-(2,2,2-trifluoroethyl)-thiourea (1) N-(4-trifluoromethylthiobenzyl)phthalimide 15.5 g of 4-trifluoromethylthiotoluene and 17.2 g of N-bromosuccinimide were added to 100 ml of benzene, and about 100 mg of 2,2'-azobisisobutyronitrile was added. The mixture was gradually heated. When the temperature reached about 86° C., the reaction solution turned red yellow. It was stirred at the same temperature for 40 minutes. The reaction solution was poured into ice water and extracted with 200 ml of ethyl acetate. The ethyl acetate solution was washed with water and dried. Ethyl acetate was evaporated under reduced pressure to give 21 g of an oily product. This product was dissolved in 50 ml of dimethylformamide, and 14.9 g of potassium phthalimide and 1 g of potassium iodide were added. The mixture was stirred at 60 oC for 1 hour. Water (50 ml) was added to the reaction solution, and the mixture was extracted with 200 ml of toluene. The toluene solution was washed with water and dried, and toluene was evaporated under reduced pressure to give 21.0 g of the captioned compound.

Melting point: 130.0–131.5° C.

IR$\nu^{KBr}_{max}$(cm$^{-1}$) 3180, 1765, 1710, 1600, 1465, 1430, 1390, 1340, 1325, 1150, 1120, 1080, 935, 735, 710.

$^1$H NMR$\delta$CDCl$_3$/TMS (ppm): 4.92(2H, s), 7.40-7.90(8H, m).

(2) 4-Trifluoromethylthiobenzyl isothiocyanate 18 g of N-(4-trifluoromethylthiobenzyl)phthalimide was dissolved in 200 ml of ethanol, and 4 g of hydrazine hydrate was added dropwise. The mixture was then heated under reflux for 3 hours, and then allowed to cool. Concentrated hydrochloric acid (10 ml) was added, and the mixture was heated under reflux for 4 hours. The precipitate formed was separated by filtration, and the ethanol solution as the filtrate was evaporated under reduced pressure. The residue was dissolved in 100 ml of water. The solution was washed with 50 ml of hexane and adjusted to pH 11 with an aqueous solution of sodium hydroxide. Ethyl acetate (100 ml) was added, and the mixture was washed with water and dried. Ethyl acetate was evaporated under reduced pressure to give 8.0 g of an oily product. The resulting product (8.0 g) was added dropwise to a mixed solution of 7.9 g of DCC, 40 ml of carbon disulfide and 20 ml of ethyl ether with stirring and ice cooling to 25° C. or below. The temperature of the mixture was returned to room temperature, and it was left to stand for 12 hours. The reaction mixture was filtered, and the residue was washed with ethyl ether and combined with the filtrate. The solvent was evaporated under reduced pressure. The resulting oily product was purified by column chromatography (silica gel; developing benzyl isothiocyanate.

IR$\nu^{neat}_{max}$(cm$^{-1}$) 2120, 1500, 1440, 1340, 1305, 1160, 1120, 1085, 1020.

$^1$H NMR $\delta$CDCl$_3$/TMS (ppm): 4.76(2H, s), 7.34(2H, d, J=9Hz), 7.66(2H, d, J=9Hz).

(3) 1-(4-Trifluoromethylthiobenzyl)-3-(2,2,2-trifluoroethylthiourea 6.0 g of 4-trifluoromethylthiobenzyl isothiocyanate obtained in (2) above and 2.5 g of 2,2,2-trifluoroethylamine was dissolved in 20 ml of ethyl acetate, and the solution was left to stand at room temperature for 24 hours. Ethyl acetate was evaporated under reduced pressure. The resulting white crystals were recrystallized from hexane to give 6.66 g of the captioned compound.

Melting point: 113.5–114.5° C.

IR $\nu^{neat}_{max}$(cm$^{-1}$) 3260, 3070, 1565, 1380, 1300, 1255, 1140, 1120, 1090, 1020, 960, 855.

$^1$H NMR $\delta$CDCl$_3$/TMS (ppm): 4.34(2H, dq, J=9Hz), 4.72(2H, J=8Hz), 6.00–6.20(1H, m), 6.60–6.80(1H, m), 7.38(2H, d, J=8Hz), 7.68(2H, d, J=8Hz).

REFERENTIAL EXAMPLE 5

Synthesis of 1-4-(2,2,2-trifluoroethoxy)benzyl)-3-(2,2,2-trifluoroethyl)thiourea Lithium aluminum hydride (2.0 g) was added to 100 ml of dry ethyl ether, and with ice cooling and ethoxy)-benzonitrile in 50 ml of dry ethyl ether was added dropwise over 30 minutes. The excess of lithium aluminum hydride was decomposed with methanol and water, and the reaction solution was extracted with 100 ml of ethyl ether. The ethyl ether solution was washed with water and dried, and ethyl ether was evaporated under reduced pressure to give 11.34 g of an oily product. A portion (5.63 g) of the resulting oily product was added dropwise to a mixture of 5.60 g of DCC, 13 ml of carbon disulfide and 30 ml of ethyl ether with stirring at −10° C. The temperature of the mixture was returned to room temperature, and it was left to stand for 12 hours. The reaction solution was filtered, and the residue was washed with ethyl ether and combined with the filtrate. The solvent was evaporated under reduced pressure. The resulting oily product was purified by column chromatography silica gel; developing solvent hexane/ethyl acetate (9:1)) to give 7.20 g of a purified product. This purified product and 4.00 g of 2,2,2-trifluoroethylamine were dissolved in 20 ml of ethyl acetate. The solution was left to stand at room temperature for 24 hours. Ethyl acetate was evaporated under reduced pressure. The resulting white crystals were recrystallized from hexane to give 9.54 g of the captioned compound.

Melting point: 119.0–120.5° C.

IR $\nu^{KBr}_{max}$(cm$^{-1}$) 3320, 3300, 1610, 1560, 1515, 1460, 1365, 1290, 1250, 1240, 1180, 1165, 1130, 1080, 975.

$^1$H NMR $\delta$Acetone-d$_6$/TMS (ppm): 4.40-4.90(6H, m), 7.01 (2H, d, J=9Hz), 7.34(2H, d, J=9Hz), 7.20–7.80 (2H, br).

REFERENT E 6

Synthesis of
1-(4-pentafluoroethylbenzyl)-3-(2,2,2-trifluoroethyl)thiourea (1) 4-pentafluoroethylbenzonitrile 15.0 g of sodium pentafluoropropionate and 15.8 g of copper iodide were dried under reduced pressure, and a solution of 4.9 g of 4-bromobenzonitrile in 80 ml of N-methylpyrrolidone was added. The reaction solution was stirred at 162 oC for 5 hours in a current of dry argon. The reaction mixture was allowed to cool, and then 300 ml of diethyl ether and 200 ml of water were added. The insoluble matter was removed by filtration. The filtrate was successively washed with water and a saturated aqueous solution of sodium chloride, and dried. Diethyl ether was evaporated under reduced pressure, and the resulting oily product was purified by column chromatography slica gel; developing solvent hexane/ethyl acetate (9:1)) to give 3.2 g of the desired 4-pentafluoroethylbenzonitrile as an oily product (yield 53.4 %).

IR $\nu^{neat}_{max}$ (cm$^{-1}$) 2215, 1410, 1345, 1330, 1280, 1205, 1155, 1100, 985, 960, 835, 740.

$^1$H NMR $\delta$CDCl$_3$/TMS (ppm): 7.70(2H, d, J$_{AB}$=8Hz), 7.84(2H, d, JAB=8Hz).

(2) 4-Pentafluoroethylbenzylamine 0.79 g of lithium aluminum hydride was suspended in 50 ml of diethyl ether, and a solution of 4.6 g of 4-pentafluoroethylbenzonitrile in 30 ml of diethyl ether was added dropwise. After the addition, the mixture was stirred at room temperature for 30 minutes, and 5 ml of water was added dropwise over 30 minutes. The insoluble matter was removed by filtration. The ether layer was dried, and then diethyl ether was evaporated under reduced pressure to give 4.7 g of the desired 4-pentafluoroethylbenzylamine as an oil.

IR $\nu^{neat}_{max}$ (cm$^{-1}$) 3350, 1610, 1575, 1470, 1415, 1340, 1285, 1200, 1140, 1090, 970, 805, 740.

$^1$H NMR $\delta$CDCl$_3$/TMS (ppm): 1.40(2H, b), 3.90(2H, b), 7.32 (2H, d, JAB=8Hz).

(3) 4-Pentafluoroethylbenzyl isothiocyanate 4.7 g of 4-pentafluoroethylbenzylamine was added dropwise to a mixture of 4.8 g of DCC, 20 ml of carbon disulfide and 50 ml of diethyl ether with stirring at −10° C. The temperature of the mixture was returned to room temperature, and it was left to stand for 12 hours.

The reaction solution was filtered, and the residue was washed with diethyl ether and combined with the filtrate. The solvent was evaporated under reduced pressure, and the resulting oily product was purified by column chromatography (silica gel; developing solvent hexane) to give 2.1 g of the desired 4-pentafluoroethylbenzyl isothiocyanate as an oil.

IR $\nu^{neat}_{max}$ (cm$^{-1}$) 2920, 2190, 2080, 1615, 1415, 1340, 1285, 1200, 1145, 1095, 970, 805, 745.

$^1$H NMR $\delta$CDCl$_3$/TMS (ppm) 4.70(2H, s), 7.30(2H, J$_{AB}$=8Hz), 7.50(2H, d, (4) 1-(4-Pentafluoroethylbenzyl)-3-(2,2,2-trifluoroethylthiourea 2.1 g of 4-pentafluoroethylbenzyl isothiocyanate and 0.78 g of 2,2,2-trifluoroethylamine were dissolved in 20 ml of ethyl acetate, and the solution was left to stand at room temperature for 24 hours. Ethyl acetate was evaporated under reduced pressure. The resulting white crystals were recrystallized from hexane to give 2.6 g of the captioned compound.

Melting point: 97.3–98.8

IR $\nu^{KBr}_{max}$ (cm$^{-1}$) 3240, 3070, 1570, 1395, 1290, 1250, 1215, 1200, 1165, 1130, 1090, 975, 935, 815, 745.

$^1$H NMR $\delta$CDCl$_3$/TMS (ppm): 4.1–4.5(2H, m), 4.74(2H, d, J=6Hz), 5.70(1H, b), 6.25(1H, b), 7.34(2H, d, J$_{AB}$=8Hz), 7.52(2H, d, JAB=8Hz).

REFERENTIAL EXAMPLE 7

Synthesis of
1-4-(2-chloro-2-propeneoxy)-benzyl)-3-(2,2,2-trifluoroethyl)thiourea (1) 4-(2-Chloro-2-propeneoxy)benzonitrile 10.0 g of 4-cyanophenol and 11.6 g of potassium carbonate were suspended in 100 ml of dimethylformamide, and 9.4 g of 2,3-dichloropropene was added dropwise. The reaction solution was stirred at 80 oC for 3 hours, allowed to cool, and poured into 200 ml of water, followed by extraction with ethyl acetate. The organic layer was washed with a saturated aqueous solution of sodium chloride and dried. Ethyl acetate was evaporated under reduced pressure. The resulting oily product was purified by column chromatography (silica gel; developing solvent hexane/ethyl acetate (9:1)) to give 15.2 g of the desired 4-(2-chloro-2-propeneoxy)benzonitrile as an oil.

Refractive index n$^{20}_D$: 1.5607.

IR $\nu^{neathd\ max}$ (cm$^{-1}$): 2210, 1630, 1600, 1570, 1505, 1450, 1300, 1255, 1225, 1165, 1040, 1020, 890, 830.

$^1$H NMR $\delta$CDCl$_3$/TMS (ppm): 4.65(2H, s), 5.46(1H, d, J=2Hz), 5.53(1H d, J=2Hz), 6.96(2H, d, JAB=10Hz), 7.56 (2H, d, JAB=10Hz).

(2) 4-(2-Chloro-2-propeneoxy)benzylamine 1 36 g of lithium aluminum hydride was suspended in 50 ml of diethyl ether, and a solution of 7.0 g of 4-(2-chloro-2-propeneoxy)benzonitrile in 40 ml of diethyl ether was added dropwise. After the addition, the mixture was stirred at room temperature for 30 minutes and then 10 ml of water was added dropwise for 30 minutes. The insoluble matter was removed by filtration. The ether layer was dried and diethyl ether was evaporated under reduced pressure to give 6.7 g of the desired 4-(2-chloro-2-propeneoxy)benzylamine as an oil.

IR $\nu^{neat}\ max$ (cm$^{-1}$) 3360, 3260, 2920, 2860, 1635, 1605, 1580, 1505, 1450, 1385, 1300, 1240, 1215, 1170, 1045, 890, 820, 715, 690.

$^1$H NMR $\delta$CDCl$_3$/TMS (ppm): 3.72(2H, b), 4.48(2H, s), 5.28 (1H d, J=2Hz), 5.40(1H, d, J=2Hz), 6.72(2H, d, J$_{AB}$=9Hz), 7.06(2H, d, J$_{AB}$=9Hz).

(3) 4-(2-Chloro-2-propeneoxy)benzyl isothiocyanate 6.7 g of 4-(2-chloro-2-propeneoxy)benzylamine was added dropwise to a mixture of 7.7 g of DCC, 20 ml of carbon disulfide and 100 ml of diethyl ether with stirring at −10° C. The temperature of the mixture was returned to room temperature, and it was left to stand for 12 hours. The reaction solution was filtered, and the residue was washed with diethyl ether and combined with the filtrate. The solvent was evaporated under reduced pressure. The resulting oily product was purified by column chromatography (silica gel; developing solvent hexane) to give 6.6 g of the desired 4-(2-chloro-2-propeneoxy)benzyl isothiocyanate as an oil.

IR$\nu^{neat}_{max}$ (cm$^{-1}$) 2160, 2070, 1690, 1640, 1610, 1510, 1450, 1445, 1350, 1300, 1245, 1220, 1170, 890, 850, 820.

$^1$H NMR $\delta$CDCl$_3$/TMS (ppm): 4.55(2H, s), 4.60(2H, s), 5.38(1H, d, J=2Hz), 5.49(1H, d, J=2Hz), 6.86 (2H, d, JAB=9Hz), 7.17(2H, d, J$_{AB}$=9Hz).

(4) 1-4-(2-chloro-2-propenoxy)benzy)-3-(2,2,2-trifluoroethyl)thiourea 6.6 g of 4-(2-chloro-2-propeneoxy)benzyl isothiocyanate and 2.7 g of 2,2,2-trifluoroethylamine were dissolved in 100 ml of ethyl acetate, and the solution was left to stand at room temperature for 24 hours. Ethyl acetate was evaporated under reduced pressure, and the resulting white crystals were recrystallized from hexane to give 5.9 g of the captined compound.

Melting point: 83.4–84.9° C.

IR $\nu^{KBr}_{max}$(cm$^{-1}$) 3240, 3070, 1605, 1565, 1505, 1380, 1350, 1295, 1250, 1225, 1165, 1115, 1040, 960, 900, 820.

$^1$H NMR δCDCl$_3$/TMS (ppm): 4.30(2H, dq, J=6Hz, 9Hz), 4.52(2H, d, J=6Hz), 4.54(2H, s), 5.40(1H, d, J=2Hz), 5.51(1H d, J=2Hz), 5.94(1H, b), 6.56 (1H, b), 6.94(2H, d, J$_{AB}$=9Hz), d, =J$_{AB}$=9Hz).

REFERENTIAL EXAMPLE 8

Synthesis of 1-[3-fluoro-4-(2,2,2-trifluoroethyl)thiourea (1) 3-Fluoro-4-(2,2,2-trifluoroethoxy)benzonitrile 2.2 g of oily sodium hydride (60 %) was suspended in 20 ml of dimethylformamide, and 5.50 g of trifluoroethanol was added dropwise at 20° C. The mixture was stirred for 1 hour, and then, a solution of 6.96 g of 4-difluorobenzonitrile in 10 ml of dimethylformamide was added dropwise. The reaction temperature rose up to 30° C. The reaction solution was stirred for 5 hours, and then 2 ml of acetic acid was added. The mixture was poured into 100 ml of ice water and extracted with toluene. The organic layer was dried and toluene was evaporated under reduced pressure. The resulting crude crystals were washed with hexane to give 10.30 g of the desired 3-fluoro-4-(2,2,2-trifluoroethoxy)benzonitrile.

Melting point: 62.0–67.0° C.

IR$\nu^{neat}_{max}$(cm$^{-1}$) 3040, 2220, 1605, 1580, 1515, 1505, 1455, 1420, 1315, 1275, 1250, 1220, 1180, 1150, 1120, 1050, 960.

$^1$H NMR δCDCl$_3$/TMS (ppm): 4.46(2H, q, J=8Hz), 7.00–7.60 (3H, m).

(2) 3-Fluoro-4-(2,2,2-trifluoroethoxy)benzyl isothiocyanate 1.40 g of lithium aluminum hydride was suspended in 50 ml of diethyl ether, and a solution of 8.00 g of 3-fluoro-4-(2,2,2-trifluoroethoxy)benzonitrile in ml of diethyl ether was added dropwise. After the addition, the mixture was stirred at room temperature for 30 minutes and subsequently, 10 ml of water was added dropwise over 30 minutes. The insoluble matter was removed by filtration. The ether layer was dried. Diethyl ether was evaporated under reduced pressure to give 7.54 g of crude 3-fluoro-4-(2,2,2-trifluoroethoxy)benzylamine as an oil.

The crude 3-fluoro-4-(2,2,2-trifluoroethoxy)benzylamine (7.54 g) was added dropwise to a mixture of 7.45 g of DCC, 15 ml of carbon disulfide and 30 ml of diethyl ether with stirring at −10° C. The temperature of the mixture was returned to room temperature, and it was left to stand for 3 hours. The reaction mixture was filtered, and the residue was washed with ethyl ether and combined with the filtrate. The solvent was evaporated under reduced pressure. The resulting oily product was purified by column chromatography (silica gel; developing 3.93 g of the desired 3-fluoro-4-(2,2,2-trifluoroethoxy)benzyl isothiocyanate.

Melting point: 38.0–40.0° C.

IR $\nu^{KBr}_{max}$(cm$^{-1}$) 2160, 2070, 1505, 1435, 1425, 1335, 1310, 1280, 1270, 1250, 1210, 1170, 1145, 1120, 1055, 960, 850.

$^1$H NMR δCDCl$_3$/TMS (ppm): 4.42(2H, q, J=8Hz), 4.65 (2H, s), 6.80–7.40(3H, m).

(3) 1-3-Fluoro-4-(2,2,2-trifluoroethoxy)benzyl]-3-(2,2,2-trifluoroethyl)thiourea 3.15 g of 3-fluoro-4-(2,2,2-trifluoroethoxy)benzyl isothiocyanate and 1.5 ml of 2,2,2-trifluoroethylamine were dissolved in 20 ml of ethyl acetate, and the solution was left to stand for 24 hours. Ethyl acetate was evaporated under reduced pressure. The resulting white crystals were recrystallized from hexane to give 3.92 g of the desired 1-[3-fluoro-4-(2,2,2-trifluoroethoxy)benzyl)-3-(2,2,2-trifluoroethyl)thiourea.

Melting point: 88.0–90.0° C.

IR $\nu^{KBr}_{max}$(cm$^{-1}$) 3260, 3080, 1600, 1570, 1525, 1440, 1390, 1350, 1310, 1290, 1270, 1255, 1195, 1180, 1165, 1135, 1125, 975.

$^1$H NMR δCDCl$_3$/TMS (ppm): 4.50(4H, q, J=9Hz), 4.81(2H, d, J=6Hz), 6.90–7.70(5H. m).

Table 3 shows the $^1$H NMR data, IR data and properties of compounds produced by methods substantially in accordance with Referential Examples 1 to 8.

TABLE 3

| (R$^2$)$_n$ | R$^3$ | $^1$H NMRδ$_{TMS}^{CDCl3}$ (ppm) | IR$\nu_{max}$ (cm$^{-1}$) | Melting point or refractive index |
|---|---|---|---|---|
| H | 4-CH$_3$ | | 3220, 3050, 1565, 1410, 1370, 1330, 1240, 1145, 1100, 1035, 960, 910, 815, 790 | Melting point 132.5–133.4° C. |
| | | | <KBr> | |
| H | 4-Cl | 4.43(2H, dq, J=6Hz, J=9Hz), 4.78(2H, d, J=9Hz), 7.39 (4H, s) | 3260, 3220, 3050, 1565, 1485, 1410, 1370, 1335, 1300, 1245, 1180, 1160, 1105, 1085, 970, 805 | Melting point 135.0–138.0° C. |
| | | <acetone-d$_6$> | <KBr> | |
| 3-Cl | 4-Cl | 4.09–4.43(2H, m), 4.57(2H, d, J=6Hz), 6.36–6.49(1H, br), 6.79–6.92(1H, br), 6.99–7.37 (4H, m) | 3290, 3140, 1590, 1490, 1415, 1390, 1350, 1325, 1270, 1200, 1185, 1130, 1050, 990, 985, 885, 845, 830, 740 | Melting point 78.0–79.7° C. |
| | | <CDCl$_3$> | <KBr> | |

TABLE 3-continued

| (R²)ₙ | R³ | ¹H NMRδ$_{TMS}^{CDCl_3}$ (ppm) | IR$\nu_{max}$ (cm⁻¹) | Melting point or refractive index |
|---|---|---|---|---|
| H | 4-O—⟨phenyl⟩ | 4.26(2H, dq, J=6.9Hz), 4.51 (2H, d, J=6Hz), 6.00(1H, brs), 6.58(1H, brs), 6.80–7.40 (9H, m) | 3240, 1585, 1550, 1530, 1500, 1480, 1370, 1350, 1245, 1160, 1145, 1115, 1100 | *Melting point 126.0–127.5° C. |
| | | <CDCl₃> | <KBr> | |
| H | 4-OCH₂—⟨phenyl⟩ | 1.00–1.90(2H, br), 4.98(2H, dq, J=6Hz, J=9Hz), 4.77(2H, d, J=5Hz), 5.13(2H, s), 6.92–7.60(9H, m) | 3250, 1610, 1570, 1510, 1380, 1350, 1315, 1295, 1255, 1220, 1160, 1150, 1110, 1020, 690 | Melting point 118.5–122.0° C. |
| | | <CDCl₃> | <KBr> | |
| H | 4-OCHF₂ | 4.16–4.47(2H, m), 4.61(2H, d, J=6Hz), 5.76(1H, b), 6.32 (1H, b), 6.52(1H, t, J=72Hz), 7.13(2H, d, J=9Hz), 7.37(2H, d, J=9Hz) | 3240, 3070, 1570, 1550, 1505, 1440, 1390, 1350, 1285, 1245, 1215, 1165, 1130, 1025, 975, 920, 860, 825, 805 | Melting point 105.5–107.9° C. |
| H | 4-OCF₂CHF₂ | 4.30(2H, dq, J=6.9Hz), 4.62 (2H, d, J=5Hz), 5.92(1H, tt, J=3.5Hz), 6.80(1H, b), 6.59 (1H, b), 7.18(2H, d, J=8Hz), 7.51(2H, d, J=8Hz) | 3220, 3070, 1570, 1560, 1535, 1515, 1375, 1310, 1280, 1260, 1220, 1200, 1165, 1120, 1095, 850 | Melting point 54.0–57.0° C. |
| | | | <KBr> | |
| H | 4-CH₂OCH₂CF₃ | 3.83(2H, q, J=9Hz), 4.41(2H, dq, J=6.9Hz), 4.63(2H, s), 4.78(2H, d, J=6Hz), 6.9–7.5 (2H, m), 7.34(4H, s) | 3280, 3230, 3070, 1570, Melting point 1395, 1380, 1340, 1305, 1270, 1250, 1185, 1170, 1135, 1110, 975 | 114.5–117.5° C. |
| | | | <KBr> | |
| H | 4-OCCl=CCl₂ | 4.37(2H, dq, J=9.6Hz), 2.65 (2H, d, J=5Hz), 5.95(1H, m), 6.51(1H, m), 7.07(2H, d, J=7Hz), 7.37(2H, d, J=7Hz) | 3220, 3060, 1590, 1565, 1495, 1375, 1340, 1305, 1290, 1280, 1245, 1200, 1185, 1155, 1140, 1120, 955, 825 | Melting point 100.0–103.9° C. |
| | | | <KBr> | |
| H | 4-SCH₂F | 4.16–4.55(2H, m), 4.77(2H, d, J=7Hz), 6.89(1H, t, J=54Hz), 7.35(2H, d, J=8Hz), 7.53(2H, d, J=8Hz), 7.64–8.05(2H, m) | 3240, 3060, 1575, 1490, 1435, 1375, 1300, 1240 | Melting point 117.5–119.0° C. |
| | | | <KBr> | |
| H | 4-SCF₂Br | 4.18–4.76(2H, m), 4.77(2H, d, J=6Hz), 6.04–6.44(1H, m), 6.65–6.96(1H, m), 7.42(2H, d, J$_{AB}$=8Hz), 7.70(2H, d, J$_{AB}$=8Hz) | 3230, 3060, 1570, 1370, 1345, 1310, 1290, 1250, 1150, 1120, 1050, 970, 930, 830, 680, 645 | Melting point 88.0–98.5° C. |
| | | | <KBr> | |
| H | 4-CF₂CF₂CF₃ | 4.21(2H, m), 4.73(2H, d, J=5Hz), 6.02(1H, m), 6.53 (1H, m), 7.20–7.60(4H, m) | 3290, 1150, 1430, 1410, 1370, 1350, 1335, 1300, 1270, 1250, 1225, 1170, 1145, 1105, 1075, 900, 820 | Melting point 65.0–67.0° C. |
| | | | <KBr> | |
| H | 4-CH₂C(CF₃)₂CF₂CF₂CF₃ | 3.53(2H, s), 4.34(2H, dq, J=9.6Hz), 4.64(2H, d, J=6Hz), 6.01(1H, m), 6.62(1H, m), 7.25(4H, s) | 3270, 1560, 1375, 1350, 1335, 1270, 1230, 1200, 1160, 1110, 1045, 980, 885, 830, 730, 700 | Melting point 53.0–56.0° C. |
| | | | <KBr> | |
| H | 4-CF₂(CF₂)₄CF₃ | 4.26(2H, m), 4.67(2H, d, J=5Hz), 5.90(1H, m), 6.40 (1H, m), 7.10–7.50(4H, m) | 3230, 3060, 1570, 1415, 1380, 1345, 1315, 1280, 1240, 1220, 1195, 1150, 1120, 1105, 1090, 1040, 1010, 970, 840 | Melting point 116.0–119.0° C. |
| | | | <KBr> | |
| H | 4-CH=CCl₂ | 4.35(2H, m), 4.64(2H, d, J=3.9Hz), 5.90(1H, b), 6.50 (1H, b), 6.83(1H, s), 7.29 (2H, d, J=8.2Hz), 7.52(2H, d, J=8.2Hz) | 3280, 3230, 3070, 1570, 1420, 1380, 1345, 1310, 1250, 1190, 1170, 1115, 1055, 980, 915, 830 | Melting point 117.0–122.0° C. |
| | | | <KBr> | |
| H | 4-COOC(CH₃)₃ | 1.59(9H, s), 4.42(2H, dq, J=6.9Hz), 4.80(2H, d, J=6Hz), 6.90(1H, b), 7.22(1H, b), 7.34(2H, d, J=8Hz), 7.87 (2H, d, J=8Hz) | 3330, 3200, 1695, 1545, 1315, 1305, 1250, 1155, 1125, 1105 | Melting point 98.0–99.0° C. |
| | | | <KBr> | |
| H | 4-O—Q⁴ | 4.25(2H, dq, J=6.9Hz), 4.60 (2H, d, J=6Hz), 6.22(1H, m), 6.57(1H, m), 7.10(2H, d, | 3320, 3180, 3030, 1600, 1560, 1555, 1540, 1460, 1400, 1380, 1330, 1310, | Melting point 137.0–141.0° C. |

TABLE 3-continued

| $(R^2)_n$ | $R^3$ | $^1H\ NMR\delta_{TMS}^{CDCl_3}$ (ppm) | $IR\nu_{max}$ (cm$^{-1}$) | Melting point or refractive index |
|---|---|---|---|---|
| | | J=9Hz), 7.35(2H, d, J=9Hz), 7.95(1H, d, J=2Hz), 8.10 (1H, b) | 1255, 1250, 1195, 1170, 1150, 1125, 1095, 1100, 1075 <KBr> | |
| H | 4-OCH$_2$CBr=CH$_2$ | 4.21–4.33(2H, m), 4.50 (2H, s), 4.59(2H, s), 5.66 (1H, s), 5.96(1H, s), 6.25 (1H, br), 6.78(1H, s), 6.85 (2H, d, J$_{AB}$=8.9Hz), 7.18(2H, d, J$_{AB}$=8.9Hz) | 3220, 1605, 1560, 1530, 1500, 1375, 1345, 1290, 1245, 1215, 1150, 1105, 1030, 900, 815, 700 <BBr> | Melting point 80.3–81.1° C. |
| H | 4-OCH$_2$CCl=CHCl (E) | 4.44–4.57(2H, m), 4.74(2H, d, J=5.4Hz), 4.91(2H, s), 6.71(1H, s), 6.95(1H, d, J$_{AB}$=8.4Hz), 7.30(2H, d, J$_{AB}$=8.4Hz), 7.35(1H, br), 7.56(1H, br) | 3260, 1565, 1535, 1515, 1380, 1255, 1225, 1170, 1120, 1040, 820, 710, 660 <KBr> | Melting point 76.8–77.7° C. |
| H | 4-OCH$_2$CCl=CHCl (Z) | 4.45–4.61(2H, m), 4.74–4.77 (2H, m), 4.81(2H, s), 6.04–7.00(3H, m), 7.31(1H, d, J$_{AB}$=8.9Hz), 7.35(1H, br), 7.59(1H, br) | 3260, 1610, 1570, 1510, 1380, 1350, 1300, 1250, 1215, 1170, 1110, 1040, 960, 830, 705, 660 <KBr> | Melting point 64.2–65.7° C. |

Q$^4$ in Table 3 shows the following structural formula.

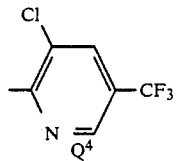

The following Formulation Examples illustrate agents comprising the compounds of geneal formula (I) produced by this invention as active ingredients and the method of producing them. The invention, however, is not limited to these examples.

FORMULATION EXAMPLE 1

Emulsifiable concentrate

| Compound produced by the invention | 10 parts |
|---|---|
| Sorpol ® 355S (tradename for a surface active agent made by Toho Chemical Co., Ltd.) | 10 parts |
| Xylene | 80 parts |

The above ingredients were mixed to form an emulsifiable concentrate.

FORMULATION EXAMPLE 2

Wettable powder

| Compound produced by the invention | 20 parts |
|---|---|
| Sodium lignosulfonate | 10 parts |
| Sodium alkylnaphthalenesulfonate | 5 parts |
| White carbon | 5 parts |
| Diatomaceous earth | 60 parts |

The above ingredients were mixed and pulverized uniformly to form a wettable powder.

FORMULATION EXAMPLE 3

Dust

Three parts of a compound in accordance with this invention was dissolved in 10 parts of acetone, and parts of clay was added. Acetone was then evaporated to give a dust.

FORMULATION EXAMPLE 4

Granules

Three parts of a compound produced by the invention, 1 part of sodium lignosulfonate, 20 parts of talc and 76 parts of bentonite were mixed, and kneaded with a moderate amount of water. The mixture was granulated and dried to give granules.

FORMULATION EXAMPLE 5

Bait

One part of a compound in accordance with this invention, 5 parts of sugar, 50 parts of wheat bran, 20 parts of rice bran and 24 parts of wheat flour were mixed and kneaded with a moderate amount of water. The mixture was then granulated and dried to give a bait.

The following Test Examples illustrate the superior insecticidal activity of the compounds of this invention. All tests were conducted through three replicates, and the results were shown by averages of the results obtained.

TEST EXAMPLE 1

Effect against tobacco cutworm

An emulsifiable concentrate prepared in accordance with Formulation Example 1 was diluted with water to a concentration of 500 ppm and 50 ppm. Cabbage leaves were immersed in the emulsions, and then air-dried. The treated leaves were transferred to a plastic cup and ten 2nd-instar larvae of tobacco cutworm were caused to feed on the treated leaves. Five days later, the mortality (%) of the insects was examined. The results are shown in Table 4.

It is seen from Table 4 that the compounds of this invention have stronger insecticidal activity than known comparative compounds of a similar structure.

TEST EXAMPLE 2

Effect against cabbage moth

An emulsifiable concentrate prepared in accordance with Formulation Example 1 was diluted with water to a concentration of 500 ppm and 50 ppm, and sprayed by a hand sprayer onto cabbage seedlings (5- to 6-leaf stage) in pots to such an extent that the chemical lightly trickled over the leaves. After air drying, the leaves were cut off and put in a plastic cup. Ten 2nd-instar larvae of cabbage moth were caused to feed on the treated leaves, and five days later, the mortality of the insects was examined. The results are shown in Table 5.

Table 5 shows that the compounds of this invention have stronger insecticidal activity than known comparative compounds of a similar structure.

TEST EXAMPLE 3

Effect against small brown planthopper

An emulsifiable concentrate prepared in accordance with Formulation Example 1 was diluted with water to a concentration of 500 ppm and 50 ppm, and sprayed by a hand sprayer onto 5 to 6 rice seedlings (3-leaf stage) to such an extent that the chemical lightly trickled over the seedlings. After air drying, the rice seedlings were held in a plastic cylinder. Ten last-instar larvae of small brown planthopper about one day after ecdysis were inoculated in the rice seedlings. The cylinder was maintained at 25 oC for 16 hours under bright conditions and for 8 hours under dark conditions. Five days later, the mortality of the insects was examined. The results are shown in Table 6.

Table 6 shows that the compounds of this invention have equivalent or stronger insecticidal activity to or than the known comparative compounds of a similar structure.

TEST EXAMPLE 4

Effect against two-spotted spider mite

An emulsifiable concentrate prepared by Formulation Example 1 was diluted with water to a concentration of 50 ppm, and sprayed perpendicularly onto 30 to 50 larvae of two-spotted spider mites obtained by incubating spider mite eggs on kidney bean leaf discs having a diameter of 3 cm and placed on wet adsorbent cotton in such an amount that the amount of the chemical on the surfaces of the leaf discs corresponded to about 2 microliters/cm². The treated mite larvae were placed in an incubator at 25° C., and four days later, the mortality of the insects was examined. The results are shown in Table 7.

It is seen from Table 7 that the compounds of this invention have equivalent or stronger acaricidal activity to or than the known comparative compounds having a similar structure.

The above Test Examples demonstrate that the compounds of this invention have stronger insecticidal activity on lepidopterous insect pests than the known comparative compounds of a similar structure, and equivalent or stronger insecticidal activity on hemipterous insect pests to or than the known comparative compounds of a similar structure; and also that the compounds of this invention have stronger acaricidal activity against mites than these comparative compounds.

TABLE 4

| Test compound No. | Mortality (%) | |
|---|---|---|
| | 500 ppm | 50 ppm |
| 6 | 100 | 100 |
| 9 | 100 | 100 |
| 12 | 100 | 100 |
| 18 | 100 | 100 |
| 27 | 100 | 100 |
| 38 | 100 | 100 |
| 40 | 100 | 100 |
| 47 | 100 | 100 |
| 71 | 100 | 100 |
| 75 | 100 | 100 |
| 76 | 100 | 100 |
| 77 | 100 | 100 |
| 82 | 100 | 100 |
| 91 | 100 | 100 |
| 93 | 100 | 100 |
| 98 | 100 | 100 |
| 99 | 100 | 100 |
| 101 | 100 | 100 |
| 120 | 100 | 100 |
| 125 | 100 | 100 |
| 166 | 100 | 100 |
| 171 | 100 | 100 |
| 172 | 100 | 100 |
| 181 | 100 | 100 |
| 186 | 100 | 100 |
| 187 | 100 | 100 |
| 193 | 100 | 100 |
| 194 | 100 | 100 |
| 215 | 100 | 100 |
| 237 | 100 | 100 |
| 258 | 100 | 100 |
| Comparative compound (a) | 0 | 0 |
| Comparative compound (b) | 100 | 20 |
| Comparative compound (e) | 0 | 0 |
| Comparative compound (f) | 0 | 0 |
| Non-treated | 0 | |

TABLE 5

| Test compound No. | Mortality (%) | |
|---|---|---|
| | 500 ppm | 50 ppm |
| 3 | 100 | 100 |
| 6 | 100 | 100 |
| 7 | 100 | 100 |
| 9 | 100 | 100 |
| 12 | 100 | 100 |
| 18 | 100 | 100 |
| 29 | 100 | 100 |
| 30 | 100 | 100 |
| 31 | 100 | 100 |
| 35 | 100 | 100 |
| 38 | 100 | 100 |
| 39 | 100 | 100 |
| 40 | 100 | 100 |
| 43 | 100 | 100 |
| 47 | 100 | 100 |
| 70 | 100 | 100 |
| 71 | 100 | 100 |
| 73 | 100 | 100 |
| 75 | 100 | 100 |
| 76 | 100 | 100 |
| 77 | 100 | 100 |
| 82 | 100 | 100 |
| 85 | 100 | 100 |
| 91 | 100 | 100 |
| 92 | 100 | 100 |
| 93 | 100 | 100 |
| 98 | 100 | 100 |
| 99 | 100 | 100 |
| 101 | 100 | 100 |
| 104 | 100 | 100 |
| 120 | 100 | 100 |
| 124 | 100 | 100 |
| 165 | 100 | 100 |

TABLE 5-continued

| Test compound No. | Mortality (%) 500 ppm | 50 ppm |
|---|---|---|
| 166 | 100 | 100 |
| 170 | 100 | 100 |
| 171 | 100 | 100 |
| 180 | 100 | 100 |
| 186 | 100 | 100 |
| 187 | 100 | 100 |
| 193 | 100 | 100 |
| 194 | 100 | 100 |
| 196 | 100 | 100 |
| 215 | 100 | 100 |
| 237 | 100 | 100 |
| 245 | 100 | 100 |
| 258 | 100 | 100 |
| 281 | 100 | 100 |
| Comparative compound (a) | 0 | 0 |
| Comparative compound (b) | 80 | 0 |
| Comparative compound (e) | 0 | 0 |
| Comparative compound (f) | 0 | 0 |
| Non-treated | 0 | |

TABLE 6

| Test compound No. | Mortality (%) 500 ppm | 50 ppm |
|---|---|---|
| 7 | 100 | 100 |
| 29 | 100 | 100 |
| 30 | 100 | 100 |
| 35 | 100 | 100 |
| 38 | 100 | 100 |
| 40 | 100 | 100 |
| 44 | 100 | 100 |
| 71 | 100 | 100 |
| 73 | 100 | 100 |
| 92 | 100 | 100 |
| 186 | 100 | 100 |
| 193 | 100 | 100 |
| 215 | 100 | 100 |
| 237 | 100 | 100 |
| Comparative compound (a) | 100 | 20 |
| Comparative compound (c) | 100 | 100 |
| Comparative compound (d) | 100 | 100 |
| Comparative compound (f) | 100 | 20 |
| Non-treated | 0 | |

TABLE 7

| Test compound No. | Mortality (%) 500 ppm |
|---|---|
| 93 | 100 |
| 98 | 100 |
| 99 | 100 |
| 101 | 100 |
| 102 | 100 |
| 120 | 100 |
| 187 | 100 |
| 193 | 100 |
| 196 | 100 |
| 220 | 100 |
| 237 | 100 |
| 245 | 100 |
| 258 | 100 |
| Comparative compound (c) | 34 |
| Non-treated | 3.7 |

Comparative compound (a) is a compound of the folllwoing formula described in Japanese Laid-Open Patent Publication No. 140577/1986.

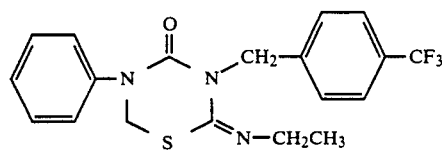

Comparative compound (b) is dichlorvos (DDVP) of the following formula:

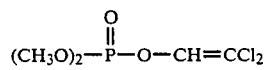

Comparative compound (c) is diazinone of the following formula:

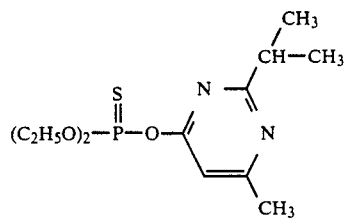

Comparative compound (d) is pyridafenthion of the following formula:

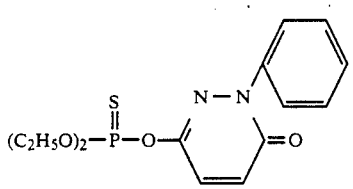

Comparative compound (e) is a compound of the following formula described in Japanese Laid-Open Patent Publication No. 3083/1979.

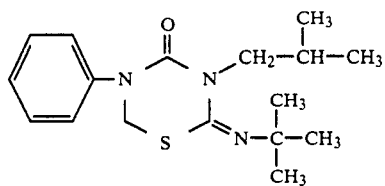

Comparative compound (f) is a compound of the following formula described in Japanese Laid-Open Patent Publication No. 140577/1986.

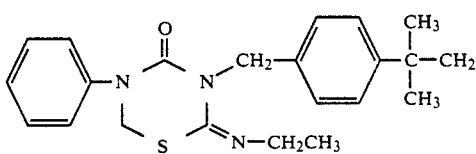

As is clearly from the foregoing statement, the tetrahydro-1,3,5-thiadiazin-4-ones of formula (I) and their salts show an excellent controlling effect on pests. Furthermore, agricultural chemical of this invention comprising the tetrahydro-1,3,5-thiadiazin-4-one of general formula (I) or its salt has excellent properties as an insecticidal and acaricidal agent and is useful.

We claim:

1. A tetrahydro-1,3,5-thiazin-4-one represented by the folllowing general formula (I)

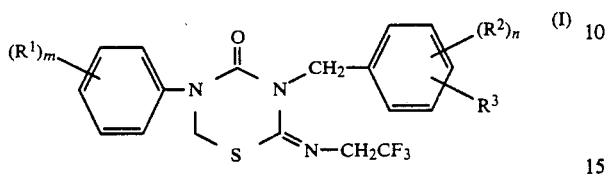

wherein each of $R^1$ and $R^2$ represents a halogen atom or an alkyl 9roup havin9 1 to 4 carbon r atoms; R3 represents a halo9en atom, an alkyl group havin9 1 to 4 carbon atoms, a cycloalkyl group having 3 to 6 carbon atoms, an alkoxy group having 1 to 4 carbon atoms, an acetyl group, a phenoxy group, a halo-substitued phenoxy group, a benzyl group, a benzyloxy group, a phenylcarbonyl group, a haloalkyloxy group having 1 to 4 carbon atoms, a haloalkyloxymethyl group having 1 to 4 carbon atoms, a haloalkenyloxy group having 2 to 4 carbon atoms, a haloalkylthio group having 1 to 4 carbon atoms, a haloalkylthiomethyl group having 1 to 4 carbon atoms, a haloalkenylthio group having 2 to 4 carbon atoms, a haloalkyl group having 1 to 8 carbon atoms, a haloalkenyl group having 2 to 8 carbon atoms, a alkyloxycarbonyl group having 1 to 8 carbon atoms, a 2,4-dichloro-phenoxycarbonyl group, or a 3-chloro-5-trifluoromethyl-2-pyridyloxy group; m represents 0, 1, 2 or 3; and n represents 0, 1, 2 or 3, or a salt thereof.

2. The compound of claim 1 in which m in formula (I) is 0.

3. The compound of claim 1 in which $R^1$ in formula (I) is a halogen atom, or an alkyl group having 1 to 4 carbon atoms.

4. The compound of claim 3 in which the halogen atom is a fluorine atom.

5. The compound of claim 4 in which the fluorine atom is substituted at the 2-position.

6. The compound of claim 3 in which the alkyl group is a methyl group.

7. The compound of claim 6 in which the methyl group is substituted at the 3-position.

8. The compound of claim 6 in which the methyl group is substituted at the 4-position.

9. The compound of claim 1 in which $R^3$ in formula (I) is a trifluoromethyl group.

10. The compound of claim 9 in which the trifluoromethyl group is substituted at the 4-position.

11. The compound of claim 1 in which $R^3$ in formula (I) is a t-butyl group.

12. The compound of claim 11 in which the t-butyl group is substituted at the 4-position.

13. The compound of claim 1 in which $R^3$ in formula (I) is a trifluoromethoxy group.

14. The compound of claim 13 in which the trifluoromethoxy group is substituted at the 4-position.

15. The compound of claim 1 in which $R^3$ in formula (I) is a pentarfluoroethyl group.

16. The compound of claim 15 in which the pentafluoroethyl group is substituted at the 4-position.

17. An insecticidal and acarididal commposition comprising at least one tetrahydro-1,3,5-thiadiazin-4-one represented by the following formula (I)

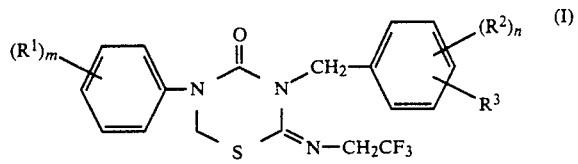

wherein each of $R^1$ and $R^2$ represents a halogen atom or an alkyl group having 1 to 4 carbon atoms; $R^3$ represents a halogen atom, an alkyl group having 1 to 4 carbon atoms, a cycloalkyl group having 3 to 6 carbon atoms, an alkoxy group having 1 to 4 carbon atoms, an acetyl group, a phenoxy group, a halo-substitued phenoxy group, a benzyl group, a benzyloxy group, a phenylcarbonyl group, a haloalkyloxy group having 1 to 4 carbon atoms, a haloalkyloxymethyl group having 1 to 4 carbon atoms, a haloalkenyloxy group having 2 to 4 carbon atoms, a haloalkylthio group having 1 to 4 carbon atoms, a haloalkylthiomethyl group hving 1 to 4 carbon atoms, a haloalkylthio group having 2 to 4 carbon atoms, a haloalkyl group having 1 to 8 carbon atoms, a haloalkenyl group having 2 to 8 carbon atoms, an alkyloxycarbonyl group having 1 to 8 carbon atoms, a 2,4-dichloro-phenoxycarbonyl group, or a 3-chloro-5-trifluoroinenthyl-2-pyridyloxy group; m represents 0, 1, 2 or 3; and n represents 0, 1, 2 or 3, or a salt thereof as an active ingredient, in admixture with a liquid or solid carrier.

18. The insecticidal and acarididal composition of claim 17 in which m in formula (I) is 9.

19. The insecticidal and acaricidal composition of claim 17 in which $R^1$ in formula (I) is a halogen atom or an alkyl group having 1 to 4 carbon atoms.

20. The insecticidal and acaricidal composition of claim 19 in which the halogen atom is a fluorine atom.

21. The insecticidal and acaricidal commposition of claim 20 in whic the fluorine atom is substituted at the 2-position.

22. The insecticidal and acaricidal composition of claim 19 in which the alkyl group is a methyl group.

23. The insecticidal and acaaricidal composition of claim 22 in which the methyl group is substituted at the 4-position.

24. The insecticidal and acaricidal composition of claim 22 in which the methyl group is substituted at the 4-position.

25. The insecticidal and acaricidal composition of claim 17 in whic $R^3$ in formula(I) is a trifluoromethyl group.

26. The insecticidal and acaricidal composition of claim 25 in whic thetrifluoromethyl group is substituted at the 4-position.

27. The insecticidal and acaricidal composition of claim 17 in which $R^3$ in formula (I) is t-butyl group.

28. The insecticidal and acaricidal composition of claim 27 in which the t-butyl group is substituted at the 4-position.

29. The insecticidal and acaricidal composition of claim 7 in which $R^3$ in formula (I) is a trifluoromethoxy group.

30. The insecticidal and acaricidal composition of claim 29 in which the trifluoromethoxy group is substituted at the 4-position.

31. The insecticidal and acaricidal composition of claim 17 in which $R^3$ in formula (I) is a pentafluoroethyl group.

32. The insecticidal and acaricidal composition of claim 31 in which the pentafluoroethyl group is substituted at 4-position.

33. A method for protecting agricultural crops from injurious insects and mites, which comprises applying to the agricultural crops or the soil where the agricultural crops are grown a protective effective amount of a tetrahydro-1,3,5-thiadiazin-4-one of claim 1.

* * * * *

UNITED STATES PATENT AND TRADEMARK OFFICE
CERTIFICATE OF CORRECTION

PATENT NO. : 5,021,412
DATED : June 4, 1991
INVENTOR(S) : NAKAYA et al.

It is certified that error appears in the above-identified patent and that said Letters Patent is hereby corrected as shown below:

Col. 50    Line two (2) of CLAIM 18 reads - - -
           claim 17 in which m in formula (I) is 9.

Col. 50    should read - - claim 17 in which m in
           formula (I) is 0.

Line three (3) of CLAIM 23 reads - - -
           4-position.

Col. 50    should read - - - 3-position.

Signed and Sealed this

Twenty-ninth Day of September, 1992

Attest:

DOUGLAS B. COMER

Attesting Officer     Acting Commissioner of Patents and Trademarks